US008622954B2

(12) United States Patent
Shahmirian et al.

(10) Patent No.: US 8,622,954 B2
(45) Date of Patent: Jan. 7, 2014

(54) RELAY DEVICE FOR TRANSFERRING INFORMATION BETWEEN A SENSOR SYSTEM AND A FLUID DELIVERY SYSTEM

(75) Inventors: Varaz Shahmirian, Northridge, CA (US); Wayne A. Morgan, Northridge, CA (US); Sheldon B. Moberg, Thousand Oaks, CA (US); Cary D. Talbot, Santa Clarita, CA (US); Arthur A. Campbell, Stevenson Ranch, CA (US); Jay A. Yonemoto, Arcadia, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 287 days.

(21) Appl. No.: 12/769,590

(22) Filed: Apr. 28, 2010

(65) Prior Publication Data

US 2010/0280442 A1 Nov. 4, 2010

Related U.S. Application Data

(63) Continuation of application No. 10/335,256, filed on Dec. 31, 2002, now abandoned.

(60) Provisional application No. 60/435,337, filed on Dec. 19, 2002.

(51) Int. Cl.
*A61M 31/00* (2006.01)
*A61B 5/00* (2006.01)

(52) U.S. Cl.
USPC .............................. 604/66; 600/347; 600/365

(58) Field of Classification Search
USPC .............. 604/131–155, 65–67; 600/345, 347, 600/365
See application file for complete search history.

(56) References Cited

U.S. PATENT DOCUMENTS 3,631,847 A    1/1972   Hobbs, II
4,212,738 A    7/1980   Henne
(Continued)

FOREIGN PATENT DOCUMENTS

DE    4329229    3/1995
EP    0098592 A2    1/1984
(Continued)

OTHER PUBLICATIONS

Bode, BW et al., "Reduction in Severe Hypoglycemia with Long-Term Continuous Subcutaneous Insulin Infusion in Type I Diabetes", Diabetes Care, vol. 19, No. 4, 324-327, (1996).

(Continued)

*Primary Examiner* — Matthew F Desanto
(74) *Attorney, Agent, or Firm* — Medtronic MiniMed, Inc.

(57) ABSTRACT

A relay device transfers information between a sensor system, which measures a physiological characteristic level of a user, and a fluid delivery system, which infuses a fluid into a user. The relay device includes a sensor system receiver for receiving communications from the sensor system in a sensor system format. The relay device also includes a processor for processing the communications from the sensor system and converting the communications for transmission in a delivery system format. The relay device further includes a delivery system transmitter for transmitting the converted communications in the delivery system format to the fluid delivery system. The sensor system and delivery system formats may utilize different frequencies and/or different communication protocols for communications transmitted between the sensor system and the fluid delivery system through the relay device.

20 Claims, 20 Drawing Sheets

(56) References Cited

U.S. PATENT DOCUMENTS

| | | | |
|---|---|---|---|
| 4,270,532 A | 6/1981 | Franetzki et al. |
| 4,282,872 A | 8/1981 | Franetzki et al. |
| 4,373,527 A | 2/1983 | Fischell |
| 4,395,259 A | 7/1983 | Prestele et al. |
| 4,433,072 A | 2/1984 | Pusineri et al. |
| 4,443,218 A | 4/1984 | DeCant, Jr. et al. |
| 4,494,950 A | 1/1985 | Fischell |
| 4,542,532 A | 9/1985 | McQuilkin |
| 4,550,731 A | 11/1985 | Batina et al. |
| 4,559,037 A | 12/1985 | Franetzki et al. |
| 4,562,751 A | 1/1986 | Nason et al. |
| 4,671,288 A | 6/1987 | Gough |
| 4,678,408 A | 7/1987 | Nason et al. |
| 4,685,903 A | 8/1987 | Cable et al. |
| 4,703,756 A | 11/1987 | Gough et al. |
| 4,731,051 A | 3/1988 | Fischell |
| 4,731,726 A | 3/1988 | Allen, III |
| 4,781,798 A | 11/1988 | Gough |
| 4,803,625 A | 2/1989 | Fu et al. |
| 4,809,697 A | 3/1989 | Causey, III et al. |
| 4,826,810 A | 5/1989 | Aoki |
| 4,871,351 A | 10/1989 | Feingold |
| 4,898,578 A | 2/1990 | Rubalcaba, Jr. |
| 4,935,105 A | 6/1990 | Churchouse |
| 4,953,552 A | 9/1990 | DeMarzo |
| 5,003,298 A | 3/1991 | Havel |
| 5,011,468 A | 4/1991 | Lundquist et al. |
| 5,019,974 A | 5/1991 | Beckers |
| 5,050,612 A | 9/1991 | Matsumura |
| 5,078,683 A | 1/1992 | Sancoff et al. |
| 5,080,653 A | 1/1992 | Voss et al. |
| 5,097,122 A | 3/1992 | Colman et al. |
| 5,100,380 A | 3/1992 | Epstein et al. |
| 5,101,814 A | 4/1992 | Palti |
| 5,108,819 A | 4/1992 | Heller et al. |
| 5,153,827 A | 10/1992 | Coutré et al. |
| 5,165,407 A | 11/1992 | Wilson et al. |
| 5,247,434 A | 9/1993 | Peterson et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,284,140 A | 2/1994 | Allen et al. |
| 5,299,571 A | 4/1994 | Mastrototaro |
| 5,307,263 A | 4/1994 | Brown |
| 5,317,506 A | 5/1994 | Coutré et al. |
| 5,320,725 A | 6/1994 | Gregg et al. |
| 5,322,063 A | 6/1994 | Allen et al. |
| 5,338,157 A | 8/1994 | Blomquist |
| 5,339,821 A | 8/1994 | Fujimoto |
| 5,341,291 A | 8/1994 | Roizen et al. |
| 5,350,411 A | 9/1994 | Ryan et al. |
| 5,356,786 A | 10/1994 | Heller et al. |
| 5,357,427 A | 10/1994 | Langen et al. |
| 5,368,562 A | 11/1994 | Blomquist et al. |
| 5,370,622 A | 12/1994 | Livingston et al. |
| 5,371,687 A | 12/1994 | Holmes, II et al. |
| 5,376,070 A | 12/1994 | Purvis et al. |
| 5,390,671 A | 2/1995 | Lord et al. |
| 5,391,250 A | 2/1995 | Cheney, II et al. |
| 5,403,700 A | 4/1995 | Heller et al. |
| 5,411,647 A | 5/1995 | Johnson et al. |
| 5,417,222 A | 5/1995 | Dempsey et al. |
| 5,482,473 A | 1/1996 | Lord et al. |
| 5,485,408 A | 1/1996 | Blomquist |
| 5,497,772 A | 3/1996 | Schulman et al. |
| 5,507,288 A | 4/1996 | Böcker et al. |
| 5,543,326 A | 8/1996 | Heller et al. |
| 5,558,640 A | 9/1996 | Pfeiler et al. |
| 5,569,186 A | 10/1996 | Lord et al. |
| 5,569,187 A | 10/1996 | Kaiser |
| 5,573,506 A | 11/1996 | Vasko |
| 5,582,593 A | 12/1996 | Hultman |
| 5,586,553 A | 12/1996 | Halili et al. |
| 5,593,390 A | 1/1997 | Castellano et al. |
| 5,593,852 A | 1/1997 | Heller et al. |
| 5,594,638 A | 1/1997 | Iliff |
| 5,609,060 A | 3/1997 | Dent |
| 5,626,144 A | 5/1997 | Tacklind et al. |
| 5,630,710 A | 5/1997 | Tune et al. |
| 5,643,212 A | 7/1997 | Coutré et al. |
| 5,660,163 A | 8/1997 | Schulman et al. |
| 5,660,176 A | 8/1997 | Iliff |
| 5,665,065 A | 9/1997 | Colman et al. |
| 5,665,222 A | 9/1997 | Heller et al. |
| 5,685,844 A | 11/1997 | Marttila |
| 5,687,734 A | 11/1997 | Dempsey et al. |
| 5,704,366 A | 1/1998 | Tacklind et al. |
| 5,750,926 A | 5/1998 | Schulman et al. |
| 5,764,159 A | 6/1998 | Neftel |
| 5,772,635 A | 6/1998 | Dastur et al. |
| 5,777,060 A | 7/1998 | Van Antwerp |
| 5,779,665 A | 7/1998 | Mastrototaro et al. |
| 5,786,439 A | 7/1998 | Van Antwerp et al. |
| 5,788,669 A | 8/1998 | Peterson |
| 5,791,344 A | 8/1998 | Schulman et al. |
| 5,807,336 A | 9/1998 | Russo et al. |
| 5,814,015 A | 9/1998 | Gargano et al. |
| 5,832,448 A | 11/1998 | Brown |
| 5,840,020 A | 11/1998 | Heinonen et al. |
| 5,861,018 A | 1/1999 | Feierbach |
| 5,868,669 A | 2/1999 | Iliff |
| 5,871,465 A | 2/1999 | Vasko |
| 5,879,163 A | 3/1999 | Brown et al. |
| 5,885,245 A | 3/1999 | Lynch et al. |
| 5,897,493 A | 4/1999 | Brown |
| 5,899,855 A | 5/1999 | Brown |
| 5,904,708 A | 5/1999 | Goedeke |
| 5,913,310 A | 6/1999 | Brown |
| 5,917,346 A | 6/1999 | Gord |
| 5,918,603 A | 7/1999 | Brown |
| 5,925,021 A | 7/1999 | Castellano et al. |
| 5,933,136 A | 8/1999 | Brown |
| 5,935,099 A | 8/1999 | Peterson et al. |
| 5,940,801 A | 8/1999 | Brown |
| 5,956,501 A | 9/1999 | Brown |
| 5,960,403 A | 9/1999 | Brown |
| 5,965,380 A | 10/1999 | Heller et al. |
| 5,972,199 A | 10/1999 | Heller et al. |
| 5,997,476 A | 12/1999 | Brown |
| 5,999,848 A | 12/1999 | Gord et al. |
| 5,999,849 A | 12/1999 | Gord et al. |
| 6,009,339 A | 12/1999 | Bentsen et al. |
| 6,032,119 A | 2/2000 | Brown et al. |
| 6,043,437 A | 3/2000 | Schulman et al. |
| 6,081,736 A | 6/2000 | Colvin et al. |
| 6,083,710 A | 7/2000 | Heller et al. |
| 6,088,608 A | 7/2000 | Schulman et al. |
| 6,101,478 A | 8/2000 | Brown |
| 6,103,033 A | 8/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Heller et al. |
| 6,162,611 A | 12/2000 | Heller et al. |
| 6,175,752 B1 * | 1/2001 | Say et al. ............... 600/345 |
| 6,183,412 B1 | 2/2001 | Benkowski et al. |
| 6,246,992 B1 | 6/2001 | Brown |
| 6,248,067 B1 | 6/2001 | Causey, III et al. |
| 6,259,937 B1 | 7/2001 | Schulman et al. |
| 6,319,241 B1 | 11/2001 | King et al. |
| 6,329,161 B1 | 12/2001 | Heller et al. |
| 6,408,330 B1 | 6/2002 | DeLaHuerga |
| 6,472,122 B1 | 10/2002 | Schulman et al. |
| 6,484,046 B1 | 11/2002 | Say et al. |
| 6,503,381 B1 | 1/2003 | Gotoh et al. |
| 6,514,718 B2 | 2/2003 | Heller et al. |
| 6,554,798 B1 | 4/2003 | Mann et al. |
| 6,558,320 B1 | 5/2003 | Causey, III et al. |
| 6,560,741 B1 | 5/2003 | Gerety et al. |
| 6,565,509 B1 | 5/2003 | Say et al. |
| 6,579,690 B1 | 6/2003 | Bonnecaze et al. |
| 6,591,125 B1 | 7/2003 | Buse et al. |

(56) References Cited

U.S. PATENT DOCUMENTS

| | | |
|---|---|---|
| 6,592,745 B1 | 7/2003 | Feldman et al. |
| 6,605,200 B1 | 8/2003 | Mao et al. |
| 6,605,201 B1 | 8/2003 | Mao et al. |
| 6,607,658 B1 | 8/2003 | Heller et al. |
| 6,616,819 B1 | 9/2003 | Liamos et al. |
| 6,618,934 B1 | 9/2003 | Feldman et al. |
| 6,623,501 B2 | 9/2003 | Heller et al. |
| 6,654,625 B1 | 11/2003 | Say et al. |
| 6,671,554 B2 | 12/2003 | Gibson et al. |
| 6,676,816 B2 | 1/2004 | Mao et al. |
| 6,689,265 B2 | 2/2004 | Heller et al. |
| 6,733,471 B1 | 5/2004 | Ericson et al. |
| 6,746,582 B2 | 6/2004 | Heller et al. |
| 6,749,740 B2 | 6/2004 | Liamos et al. |
| 6,809,653 B1 | 10/2004 | Mann et al. |
| 6,881,551 B2 | 4/2005 | Heller et al. |
| 6,893,545 B2 | 5/2005 | Gotoh et al. |
| 6,916,159 B2 | 7/2005 | Rush et al. |
| 6,932,894 B2 | 8/2005 | Mao et al. |
| 6,942,518 B2 | 9/2005 | Liamos et al. |
| 2002/0082665 A1 | 6/2002 | Haller et al. |
| 2002/0161288 A1 | 10/2002 | Shin et al. |
| 2003/0078560 A1 | 4/2003 | Miller et al. |
| 2003/0088166 A1 | 5/2003 | Say et al. |
| 2003/0152823 A1 | 8/2003 | Heller |
| 2003/0168338 A1 | 9/2003 | Gao et al. |
| 2003/0176183 A1 | 9/2003 | Drucker et al. |
| 2003/0188427 A1 | 10/2003 | Say et al. |
| 2003/0199744 A1 | 10/2003 | Buse et al. |
| 2003/0220552 A1 | 11/2003 | Reghabi et al. |
| 2004/0061232 A1 | 4/2004 | Shah et al. |
| 2004/0061234 A1 | 4/2004 | Shah et al. |
| 2004/0064133 A1 | 4/2004 | Miller et al. |
| 2004/0064156 A1 | 4/2004 | Shah et al. |
| 2004/0074785 A1 | 4/2004 | Holker et al. |
| 2004/0093167 A1 | 5/2004 | Braig et al. |
| 2004/0111017 A1 | 6/2004 | Say et al. |
| 2004/0122353 A1 | 6/2004 | Shahmirian et al. |
| 2005/0214585 A1 | 9/2005 | Bernatz et al. |
| 2010/0280442 A1 | 11/2010 | Shahmirian et al. |

FOREIGN PATENT DOCUMENTS

| | | |
|---|---|---|
| EP | 0098592 A3 | 8/1985 |
| EP | 0319268 B1 | 6/1989 |
| EP | 0680727 B1 | 11/1995 |
| EP | 0806738 A1 | 11/1997 |
| EP | 0880936 A2 | 12/1998 |
| EP | 0880936 A3 | 3/1999 |
| EP | 1048264 A1 | 11/2000 |
| EP | 1338295 A1 | 8/2003 |
| GB | 2218831 | 11/1998 |
| WO | 9849659 A3 | 11/1989 |
| WO | 9528878 A1 | 11/1995 |
| WO | 9620745 A1 | 7/1996 |
| WO | 9636389 A1 | 11/1996 |
| WO | 9637246 A1 | 11/1996 |
| WO | 9721456 A1 | 6/1997 |
| WO | 9728736 A1 | 8/1997 |
| WO | 9820439 A1 | 5/1998 |
| WO | 9824358 A2 | 6/1998 |
| WO | 9824358 A3 | 6/1998 |
| WO | 9842407 A1 | 10/1998 |
| WO | 9849659 A2 | 11/1998 |
| WO | 9856293 A1 | 12/1998 |
| WO | 9859487 A1 | 12/1998 |
| WO | 9908183 A1 | 2/1999 |
| WO | 9910801 A1 | 3/1999 |
| WO | 9918532 A1 | 4/1999 |
| WO | 9922236 A1 | 5/1999 |
| WO | 9945375 A1 | 9/1999 |
| WO | 9945387 A2 | 9/1999 |
| WO | 9945387 A3 | 9/1999 |
| WO | 9956613 A1 | 11/1999 |
| WO | 0010628 A2 | 3/2000 |
| WO | 0010628 A3 | 3/2000 |
| WO | WO 0010628 * | 3/2000 |
| WO | 0019887 A1 | 4/2000 |
| WO | 0047109 A1 | 8/2000 |
| WO | 0048112 A2 | 8/2000 |
| WO | 0048112 A3 | 8/2000 |
| WO | 0078210 A1 | 12/2000 |
| WO | 0128416 A1 | 4/2001 |
| WO | 0128495 A2 | 4/2001 |
| WO | 0128495 A3 | 4/2001 |
| WO | 0139089 A1 | 5/2001 |
| WO | 0152718 A2 | 7/2001 |
| WO | 0152718 A3 | 7/2001 |
| WO | 0152727 A1 | 7/2001 |
| WO | WO 0152727 * | 7/2001 |
| WO | 0156454 A2 | 8/2001 |
| WO | 0156454 A3 | 8/2001 |
| WO | 02058537 A9 | 8/2002 |

OTHER PUBLICATIONS

Boland, E, Teens Pumping it Up! Insulin Pump Therapy Guide for Adolescents, 2nd Edition, (1998).

Brackenridge, BP, "Carbohydrate Gram Counting A Key to Accurate Mealtime Boluses in Intensive Diabetes Therapy", Practical Diabetology, vol. 11, No. 2, pp. 22-28, (1992).

Brackenridge, BP et al., Counting Carbohydrates How to Zero in on Good Control using the MiniMed insulin pump, MiniMed Technologies Inc., (1995).

Farkas-Hirsch, R et al. "Continuous Subcutaneous Insulin Infusion: A Review of the Past and Its Implementation for the Future", Diabetes Spectrum From Research to Practice, vol. 7, No. 2, pp. 80-84, 136-138, (1994).

Hirsch, IB et al., "Intensive Insulin Therapy for Treatment of Type I Diabetes", Diabetes Care, vol. 13, No. 12, pp. 1265-1283, (1990).

Kulkarni, K et al., "Carbohydrate Counting A Primer for Insulin Pump Users to Zero in on Good Control", MiniMed Inc., (1999).

Marcus, AO et al., "Insulin Pump Therapy Acceptable Alternative to Injection Therapy", Postgraduate Medicine, vol. 99, No. 3, pp. 125-143 (1996).

Reed, J, "Living with Diabetes", Voice of the Diabetic, vol. 11, No. 3, pp. 1-38, (1996).

Skyler, JS, "Continuous Subcutaneous Insulin Infusion [CSII] With External Devices: Current Status", Update in Drug Delivery Systems, Futura Publishing Company, Chapter 13, pp. 163-183, (1989).

Skyler, JS et al., The Insulin Pump Therapy Book Insights from the Experts, MiniMed Technologies, (1995).

Strowig, SM, "Initiation and Management of Insulin Pump Therapy", The Diabetes Educator, vol. 19, No. 1, pp. 50-60 (1993).

Walsh, J et al., Pumping Insulin: The Art of Using an Insulin Pump, Published by MiniMed Technologies, (1989).

(Intensive Diabetes Management, 1995). Insulin Infusion Pump Therapy. pp. 66-78.

International Search Report for International Application No. PCT/US02/03299 filed Feb. 5, 2002.

International Search Report for International Application No. PCT/US01/01670 filed Jan. 17, 2001.

Reach, G et al., "A Method for Evaluating in vivo the Functional Characteristics of Glucose Sensors", Biosensors 2 (Elsevier Applied Science Publishers Ltd., England, pp. 211-220, (1986).

Koudelka, M et al., "Planar Amperometric Enzyme-Based Glucose Microelectrode", Sensors and Actuators, 18 (Elsevier Sequoia, The Netherlands, pp. 157-165, (1989).

Gernet, S et al., "A Planar Glucose Enzyme Electrode", Sensors and Actuators, 17 (Elsevier Sequoia, The Netherlands), pp. 537-540, (1989).

Velho, G et al., "Strategies for calibrating a subcutaneous glucose sensor", Biomed. Biochim. Acta 48, pp. 957-964, (1989.

Koudelka, M et al., "In-vivo Behaviour of Hypodermically Implanted Microfabricated Glucose Sensors", Biosensors & Bioelectronics 6, (Elsevier Science Publishers Ltd., England), pp. 31-36, (1991).

(56) References Cited

OTHER PUBLICATIONS

Mastrototaro, JJ et al., "An electroenzymatic glucose sensor fabricated on a flexible substrate", Sensors and Actuators B. 5, (Elsevier Sequoia), pp. 139-144, (1991).
Rebrin, K et al., "Subcutaneous glucose predicts plasma glucose independent of insulin: implications for continuous monitoring", The American Physiological Society, pp. E561-E571, (1999).
International Search Report for International Application No. PCT/US03/22862 filed Jul. 23, 2003.
Furler, SM et al., "Development and testing of a simple algorithm for a glucose clamp", Medical & Biological Engineering & Computing, (vol. 24, No. 4, pp. 365-370, XP0022589180, ISSN: 0140-0118, p. 367, left hand column, line 23-29), (Jul. 1986—Australia).
Abel, P. et al., "Experience with an implantable glucose sensor as a prerequisite of an artificial beta cell", Biomed. Biochim. Acta 43 (1984) 5, pp. 577-584.
Boguslavsky, L. et al., "Applications of redox polymers in biosensors", Solid State Ionics (Elsevier Science Publishers B.V., North-Holland), (1993), pp. 189-197.
Geise, Robert J. et al., "Electropolymerized 1,3-diaminobenzene for the construction of a 1,1'-dimethylferrocene mediated glucose biosensor", Analytica Chimica Acta, 281 (Elsevier Science Publishers B.V., Amsterdam), (1993), pp. 467-473.
Gernet, S. et al., "Fabrication and Characterization of a Planar Electrochemical Cell and Its Application as a Glucose Sensor", Sensors and Actuators, 18 (Elsevier Sequoia, The Netherlands—1989), pp. 59-70.
Kanapieniene, J.J., "Miniature glucose biosensor with extended linearity", Sensors and Actuators B. 10, (Elsevier Sequoia), (1992), pp. 37-40.
Gorton, L. et al., "Amperometric glucose sensors based on immobilized glucose-oxidizing enzymes and chemically modified electrodes", Analytica Chimica Acta, 249 (Elsevier Science Publishers BV, Amsterdam), (1991), pp. 43-54.
Gorton, L. et al., "Amperometric Biosensors Based on an Apparent Direct Electron Transfer Between Electrodes and Immobilized Peroxidases", (Plenary Lecture at Department of Analytical Chemistry, University of Lund—Sweden), (Aug. 1992), vol. 117, pp. 1235-1241.
Gough, D. et al., "Two-Dimensional Enzyme Electrode Sensor for Glucose", (American Chemical Society), Reprinted from Analytical Chemistry (1985) 57, pp. 2351-2357.
Gregg, B. et al., "Cross-Linked Redox Gels Containing Glucose Oxidase for Amperometric Biosensor Applications", Anal. Chem. 62, (Department of Chemical Engineering, University of Texas, Austin), (American Chemical Society), (1990), pp. 258-263.
Gregg, B. et al., Redox Polymer Films Containing Enzymes. 1. A Redox-Conducting Epoxy Cement: Synthesis, Characterization, and Electrocatalytic Oxidation of Hydroquinone, J. Phys. Chem. 95, (1991), pp. 5970-5975.
Heller, A., "Electrical Wiring of Redox Enzymes", Accounts of Chemical Research, (American Chemical Society), (May 1990) (vol. 23, No. 5), pp. cover, 128-134.
Johnson K.W. et al., "In vivo evaluation of an electroenzymatic glucose sensor implanted in subcutaneous tissue", Biosensors & Bioelectronics 7, (Elsevier Science Publishers Ltd.), (1992), pp. 709-714.
Jönsson, G. et al., "An Electrochemical Sensor for Hydrogen Peroxide Based on Peroxidase Adsorbed on a Spectrographic Graphite Electrode", Electroanalysis 1, (VCH Publishers, Inc.), (1989), pp. 465-468.
Kawamori, R. et al., "Perfect Normalization of Excessive Glucagon Responses to Intravenous Arginine in Human Diabetes Mellitus with the Artificial Beta-Cell", Rapid Publication from Diabetes, vol. 29, (Sep. 1980), pp. 762-765.
Kimura, J. et al., "An Immobilized Enzyme Membrane Fabrication Method using an Ink Jet Nozzle", Biosensors 4, (Elsevier Science Publishers Ltd.—England), (1988), pp. 41-52.
Mastrototaro, John J. et al., "An Electroenzymatic Sensor Capable of 72 Hour Continuous Monitoring of Subcutaneous Glucose", Presentation given at the 14th International Diabetes Federation Congress in Washington, D.C., (Jun. 23-28, 1991), 19 pages.
McKean, B., et al., "A Telemetry-Instrumentation System for Chronically Implanted Glucose and Oxygen Sensors", IEEE Transactions on Biomedical Engineering, (Jul. 1988), vol. 35, No. 7, pp. 526-532.
Monroe, D. et al., "Novel implantable glucose sensors", ACL, (Dec. 1989), pp. 8-16.
Morff, R.J. et al., "Microfabrication of Reproducible, Economical, Electroenzymatic Glucose Sensors", Annual International Conference of IEEE Engineering in Medicine and Biology Society, (1990), vol. 12, No. 2, pp. 0483-0484.
Nakamoto, S. et al., "A Lift-Off Method for Patterning Enzyme-Immobilized Membranes in Multi-Biosensors", Sensors and Actuators, 13, (Elsevier Sequoia), (1988), pp. 165-172.
Nishida, K. et al., "Clinical applications of the wearable artificial endocrine pancreas with the newly designed needle-type glucose sensor", (Elsevier Science B.V.), (1994), pp. 353-358.
Shichiri, M. et al., "An artificial endocrine pancreas—problems awaiting solution for long-term clinical applications of a glucose sensor", Frontiers Med. Biol. Engng, (VSP), (1991), vol. 3., No. 4, pp. 283-292.
Shichiri, M. et al., "Wearable Artificial Endocrine Pancreas with Needle-Type Glucose Sensor", The Lancet, (Nov. 20, 1982), pp. 1129-1131.
Shichiri, M. et al., "Telemetry Glucose Monitoring Device with Needle-Type Glucose Sensor: A Useful Tool for Blood Glucose Monitoring in Diabetic Individuals", Diabetes Care, (May-Jun. 1986), vol. 9, No. 3, pp. 298-301.
Shichiri, M. et al., "Normalization of the Paradoxic Secretion of Glucagon in Diabetics Who Were Controlled by the Artifical Beta Cell", Diabetes, (Apr. 1979), vol. 28, pp. 272-275.
Shichiri, M. et al., "Closed-Loop Glycemic Control with a Wearable Artificial Endocrine Pancreas Variations in Daily Insulin Requirements to Glycemic Response", Rapid Publication from Diabetes, vol. 33, (Dec. 1984), pp. 1200-1202.
Shichiri, M. et al., "In Vivo Characteristics of Needle-Type Glucose Sensor—Measurements of Subcutaneous Glucose Concentrations in Human Volunteers-", Hormone and Metabolic Research, (Thieme Medical Publishers, Inc.), Supplement Series vol. No. 20, (1988), pp. 17-20.
Shichiri, M. et al., "A Needle-Type Glucose Sensor—A Valuable Tool Not Only for a Self-Blood Glucose Monitoring But for a Wearable Artificial Pancreas-", Life Support Systems, Proceedings XI Annual Meeting ESAO Alpbash-Innsbruck Austria, (Sep. 1984), vol. 2, Supplement 1, pp. 7-9.
Shichiri, M. et al., "The Wearable Artificial Endocrine Pancreas with a Needle-Type Glkucose Sensor: Perfect Glycemic Control in Ambulatory Diabetics", Acta Paediatr Jpn 26, (1984), pp. 359-370.
Shichiri, M. et al., "Glycaemic Control in Pancreatectomized Dogs with a Wearable Artificial Endocrine Pancreas", Diabetologica 24, (1983), pp. 179-184.
Shichiri, M. et al., "Membrane design for extending the long-life of an implantable glucose sensors", Diab. Nutr. Metab. 2, vol. 2, No. 4, (1989), pp. 309-313.
Shinkai, S et al., "Molecular Recognition of Mono- and Di-saccharides by Phenylboronic Acids in Solvent Extraction and as a Monolayer", J. Chem. Soc., Chem. Commun., (1991), pp. 1039-1041.
Tamiya, E. et al., "Micro Glucose Sensors Using Electron Mediators Immobilized on a Polypyrrole-Modified Electrode", Sensors and Actuators, 18, (Elsevier Sequoia), (1989), pp. 297-307.
Tsukagoshi, K. et al., "Specific Complexation with Mono- and Disaccharides that can be Detected by Circular Dichroism", J. Org. Chem 56, (1991), pp. 4089-4091.
Urban, G. et al., "Miniaturized multi-enzyme biosensors integrated with pH sensors on flexible polymers carriers for in vivo applications", Biosensors & Bioelectronics 7, (Elsevier Science Publishers Ltd.), (1992), pp. 733-739.
Urban, G. et al, "Miniaturized thin-film biosensors using covalently immobilized glucose oxidase", Biosensors & Bioelectronics 6, (Elsevier Science Publishers Ltd.), (1991), pp. 555-562.

(56) References Cited

OTHER PUBLICATIONS

Velho, G. et al., "In vivo calibration of a subcutaneous glucose sensor for determination of subcutaneous glucose kinetics", Diab. Nutr. Metab. 3 (1988), pp. 227-233.

Yokoyama, K., "Integrated Biosensor for Glucose and Galactose", Analytica Chimica Acta, 218, (Elsevier Science Publishers B.V.—Amsterdam), (1989), pp. 137-142.

Nishida, K. et al., "Development of a ferrocene-mediated needle-type glucose sensor covered with newly designed biocompatible membrane, 2-methacryloyloxyethyl phosphorylcholine-co-n-butyl methacrylate", Medical Progress through Technology 21, (Kluwer Academic Publishers), (1995), pp. 91-103.

Yamasaki, Y. et al., "Direct measurement of whole blood glucose by a needle-type sensor", Clinica Chimica Acta, 93, (Elsevier Science Publishers B.V.), (1989), pp. 93-98.

Sternberg, R. et al., "Study and Development of Multilayer Needle-type Enzyme-based Glucose Microsensors", Biosensors 4, (Elsevier Science Publishers Ltd—England), (1988), pp. 27-40.

Shaw, G.W. et al., "In vitro testing of a simply constructed, highly stable glucose sensor suitable for implantation in diabetic patients", Biosensors & Bioelectronics 6, (Elsevier Publishers Ltd—England), (1991), pp. 401-406.

Poitout, V. et al., "A glucose monitoring system for on line estimation in man of blood glucose concentration using a miniaturized glucose sensor implanted in the subcutaneous tissue and a wearable control unit", Diabetologia 36, (1993), pp. 658-663.

Hashiguchi, Y. et al., "Development of a Miniaturized Glucose Monitoring System by Combining a Needle-Type Glucose Sensor with Microdialysis Sampling Method Long-term subcutaneous tissue glucose monitoring in ambulatory diabetic patients", Diabetes Care, (1994), vol. 17, No. 5, pp. 387-389.

Jobst, G. et al., "Thin-Film Microbiosensors for Glucose-Lactate Monitoring", Anal. Chem. 68, (American Chemical Society), (1996), vol. 68, No. 18, pp. 3173-3179.

Shults, M.C. et al., "A Telemetry-Instrumentation System for Monitoring Multiple Subcutaneously Implanted Glucose Sensors", IEEE Transactions on Biomedical Engineering, (1994), vol. 41, No. 10, pp. 937-942.

Wang, J. et al., "Needle-Type Dual Microsensor for the Simultaneous Monitoring of Glucose and Insulin", Analytical Chemistry, (Feb. 15, 2001), vol. 73, No. 4, pp. 844-847.

Moussy, F. et al., "Performance of Subcutaneously Implanted Needle-Type Glucose Sensors Employing a Novel Trilayer Coating", Anal. Chem., 65, (American Chemical Society), (1993), pp. 2072-2077.

Bindra, D.S. et al., "Design and in Vitro studies of a Needle-Type Glucose Sensor for Subcutaneous Monitoring", Anal. Chem., 63, (American Chemical Society), (1991), pp. 1692-1696.

\* cited by examiner

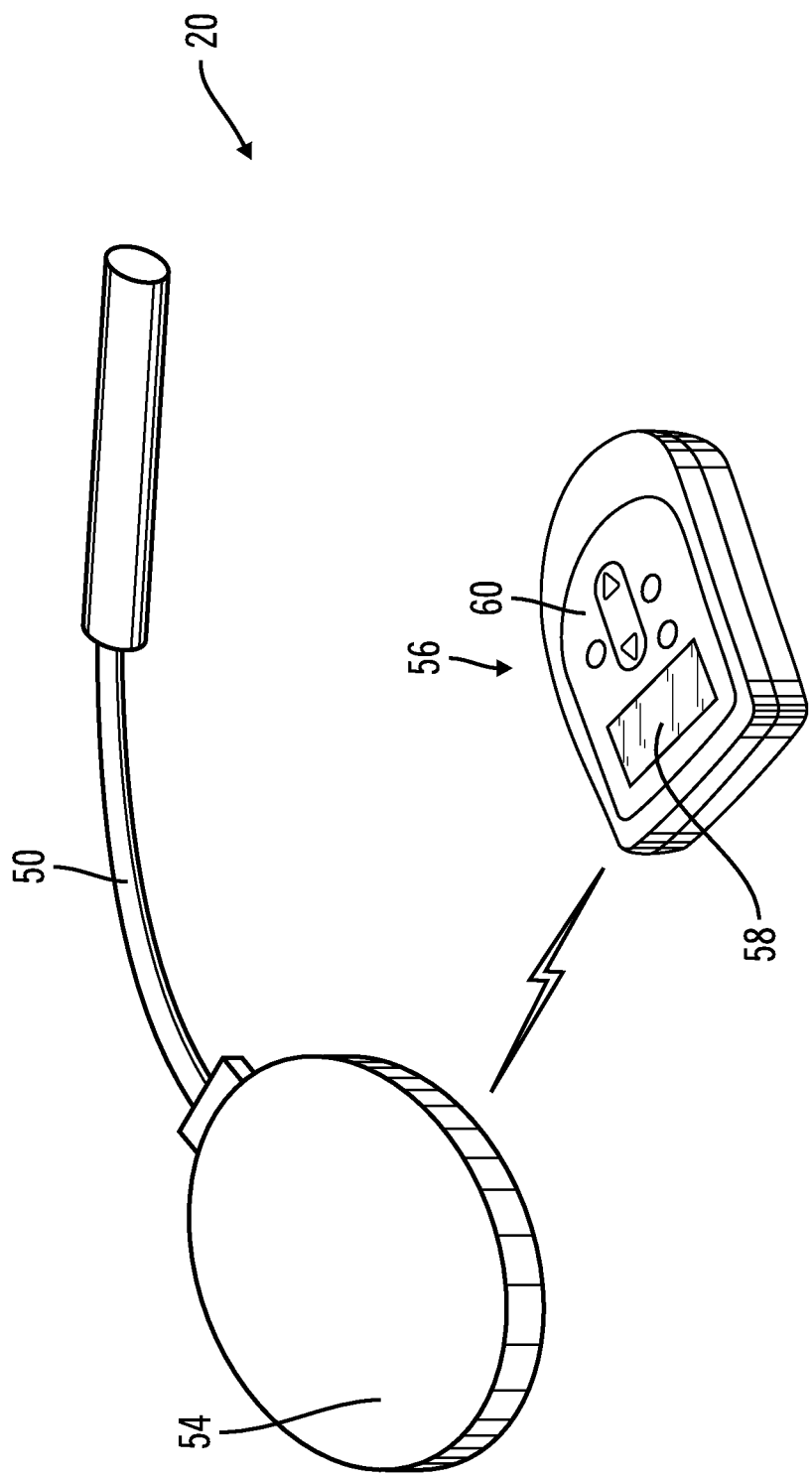

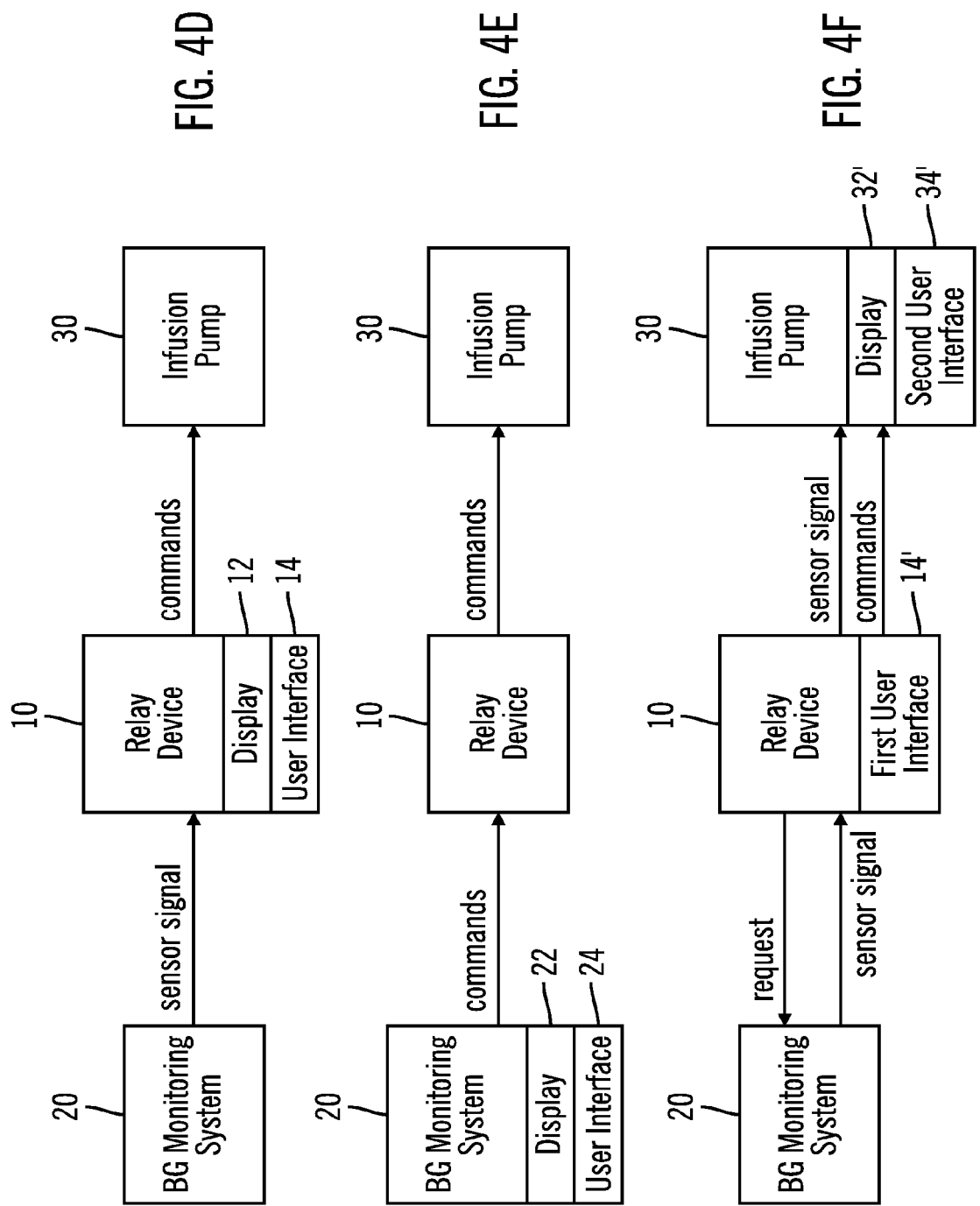

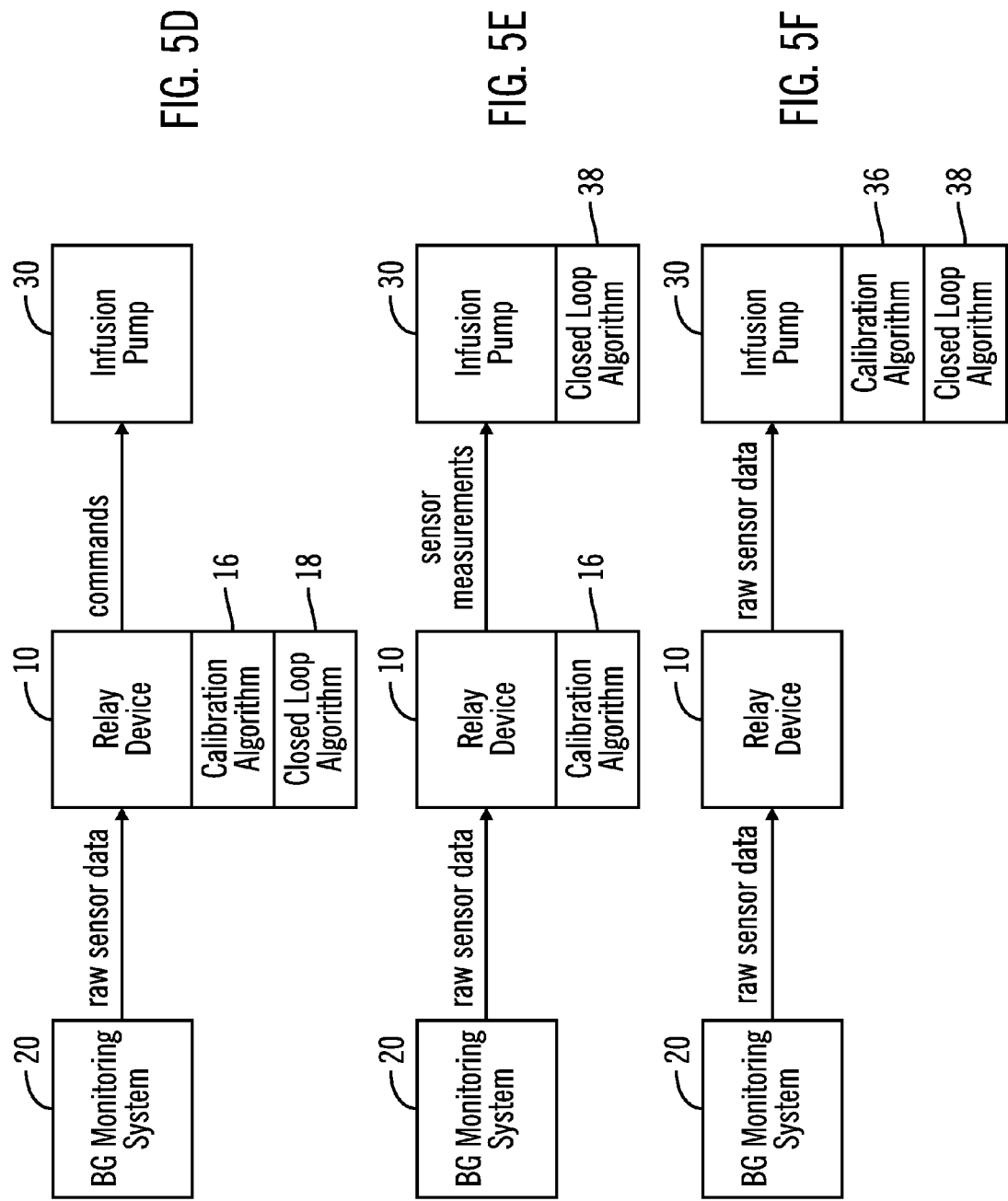

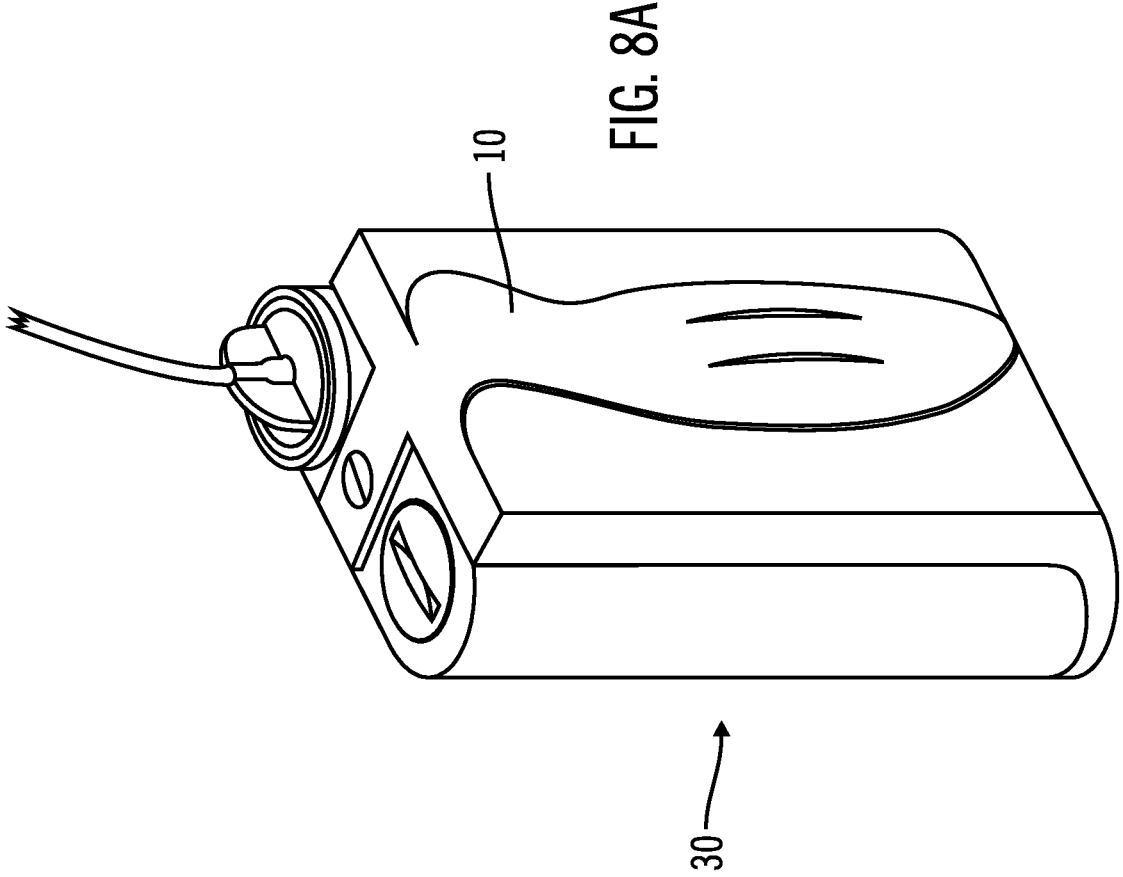

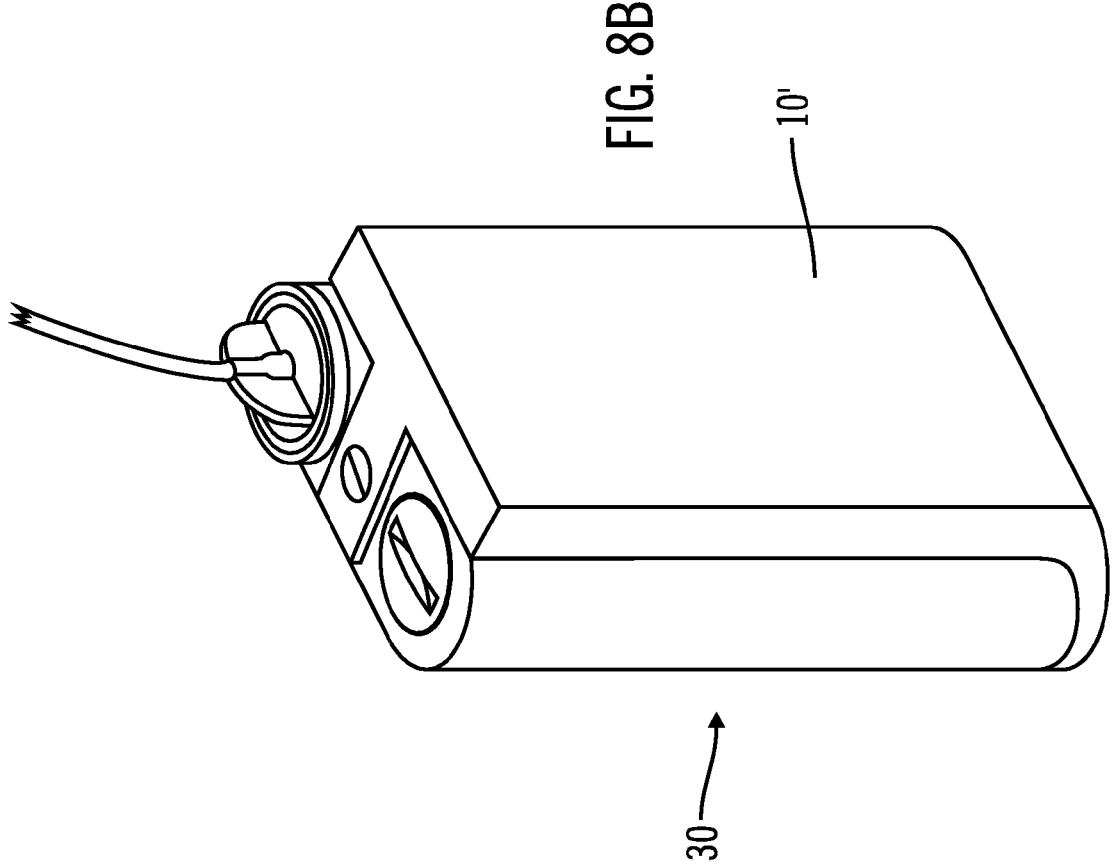

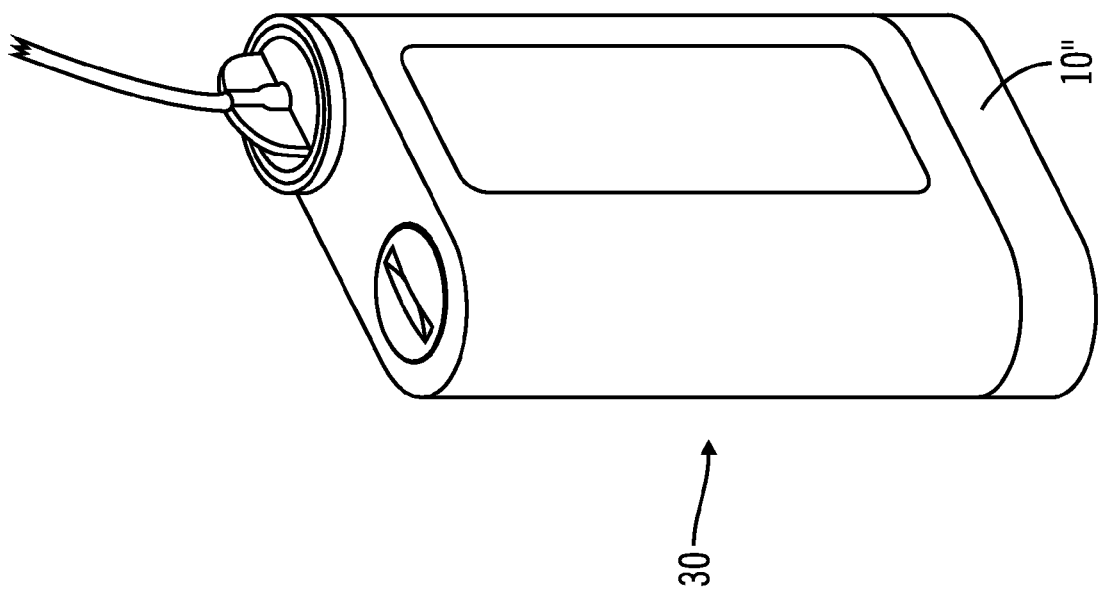

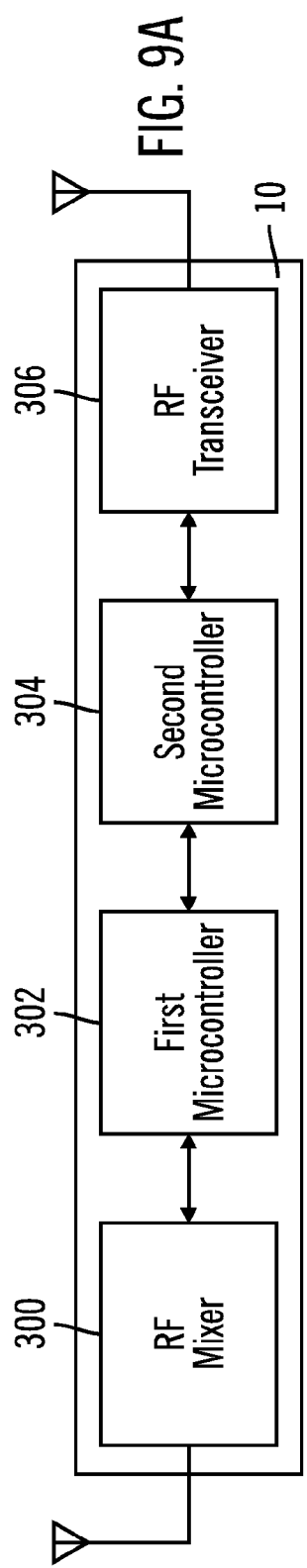
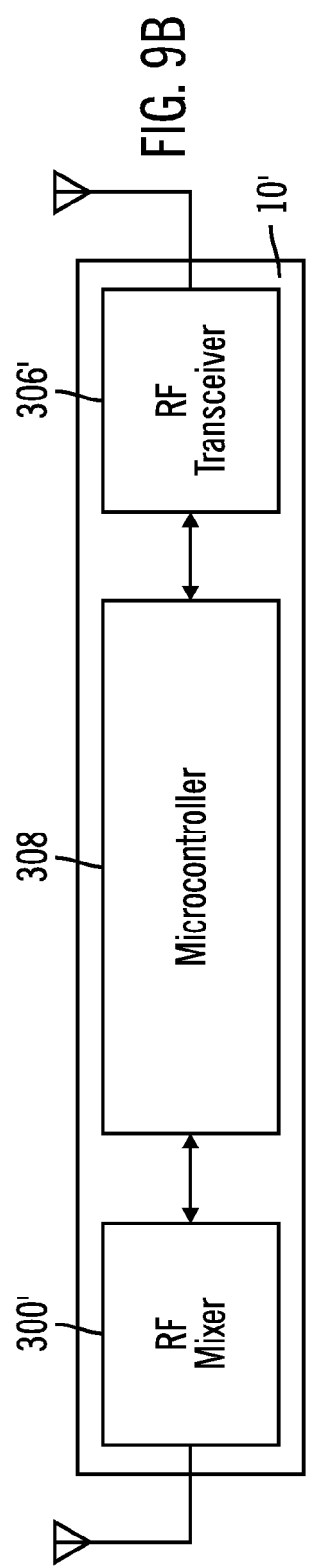
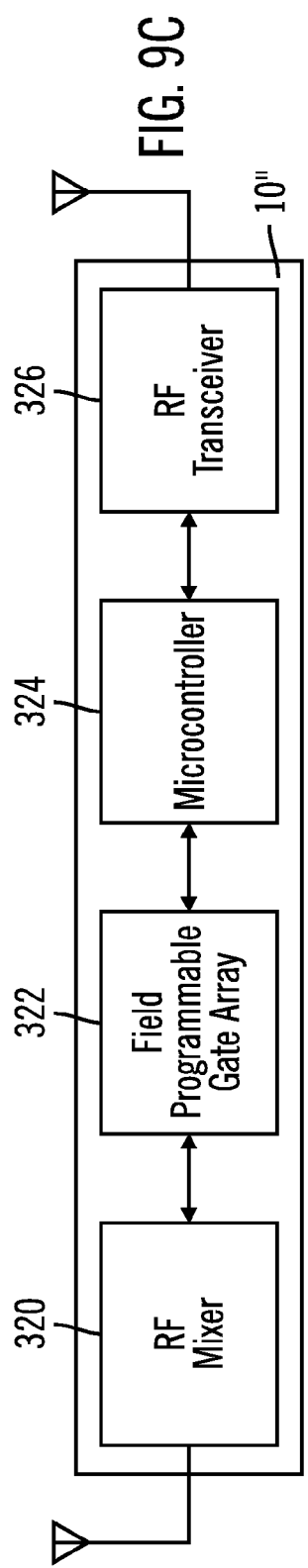
FIG. 9A
FIG. 9B
FIG. 9C

RELAY DEVICE FOR TRANSFERRING INFORMATION BETWEEN A SENSOR SYSTEM AND A FLUID DELIVERY SYSTEM

RELATED APPLICATIONS

This application is a continuation application of U.S. patent application Ser. No. 10/335,256, filed Dec. 31, 2002, which claims priority on U.S. Provisional Patent Application filed Dec. 19, 2002 and entitled "Relay Device for Transferring Information Between a Sensor System and a Fluid Delivery System," which is herein specifically incorporated by reference.

BACKGROUND OF THE INVENTION

Ambulatory pumps and hospital-based fluid delivery systems are used to deliver fluids into the bodies of patients. For some therapies, sensor measurements of a patient's physiological characteristics are used to calculate fluid dosage requirements. Typically, a sensor monitor is used to collect sensor data from a sensor, calibrate the sensor data to generate sensor measurements, and display the sensor measurements. Next, the patient or a caregiver manually calculates the required fluid dosage based on the displayed sensor measurements. Finally, the patient or caregiver programs the pump or fluid delivery system to adjust the fluid dosage.

For example, patients with Type 1 diabetes and some patients with Type 2 diabetes use insulin to control their blood glucose (BG) level. Typically, if a patient's BG level is too high, the patient can inject a "bolus" (dose) of insulin to lower his/her BG level from its present level to a desired target level. Furthermore, the patient may inject a bolus of insulin in anticipation of ingesting carbohydrates, thus heading off a sharp rise in his/her BG level. Presently, a patient or caregiver must measure the patient's blood glucose using a BG monitoring system, such as a continuous glucose measurement system, a test strip meter, a hospital-based measurement system, or an automated intermittent blood glucose measurement system. When the BG monitoring system has generated a BG measurement, the BG measurement is displayed on the BG monitoring system. Next, the patient or caregiver must visually read and then utilize the BG measurement to manually calculate a required insulin bolus (i.e., the amount of insulin to inject). Finally, once the required insulin bolus is calculated, the patient or caregiver must utilize an insulin delivery device (e.g., infusion pump, injection pen, IV meter, or the like) to deliver the insulin bolus into the patient's body.

Unfortunately, this process requires the patient or caregiver to handle several pieces of equipment, including the BG monitoring system and the insulin delivery device, which may discourage the patient or caregiver from using the BG measurements to adjust the insulin dosage, and thus, decrease the efficacy of the insulin delivery device. Additionally, if the BG monitoring system and the insulin delivery device are not developed in conjunction with one another, they typically communicate using different frequencies and/or modes of communication, and as a result, cannot communicate directly with one another. Thus, the patient or caregiver must manually calculate the required insulin bolus and program the insulin delivery device accordingly, which requires effort by the patient or caregiver and is subject to calculation errors. Alternatively, the patient or caregiver must manually enter the BG measurement into an electronic computing device with bolus estimation software for calculating the required insulin bolus (e.g., a computer, the Internet, a personal digital assistant (PDA), or an insulin delivery device, such as an infusion pump, injection pen, IV meter, or the like), which also requires effort by the patient or caregiver and is subject to transcription errors. For example, the patient or caregiver may not accurately enter the BG measurement that is displayed on the BG measurement device into the electronic computing device, and thus, the resulting bolus estimate calculation may not be accurate.

SUMMARY OF THE INVENTION

It is an object of an embodiment of the present invention to provide an improved infusion system including a relay device for transferring information between a sensor system and a fluid delivery system, which obviates for practical purposes, the above mentioned limitations.

According to an embodiment of the invention, an infusion system for infusing a fluid into a user includes a sensor system, a relay device, and a delivery system. The sensor system includes a sensor system housing, a sensor coupled to the sensor system housing for producing a signal indicative of a physiological characteristic level of the user, a sensor system processor contained in the sensor system housing for processing the signal indicative of the physiological characteristic level of the user, and a sensor system transmitter contained in the sensor system housing and coupled to the sensor system processor for transmitting one or more communications in a sensor system format. The relay device includes a relay device receiver for receiving the communications from the sensor system in the sensor system format, a relay device processor for processing the communications from the sensor system and converting the communications for transmission in a delivery system format, and a relay device transmitter for transmitting the converted communications in the delivery system format. The fluid delivery system includes a delivery system housing, a delivery system receiver contained in the delivery system housing for receiving the communications from the relay device in the delivery system format, and a delivery system processor contained in the delivery system housing and coupled to the delivery system receiver for processing the communications from the relay device in the delivery system format and controlling an amount of the fluid infused into the user. Further, the amount of the fluid infused into the user is determined based upon data indicative of the physiological characteristic level of the user.

In particular embodiments, at least one of the communications transmitted from the sensor system through the relay device and received by the fluid delivery system include data indicative of the physiological characteristic level of the user. Additionally, the communications including the data indicative of the physiological characteristic level of the user may be automatically transmitted from the sensor system through the relay device and received by the fluid delivery system. Further, the fluid delivery system may also include a display device contained in the delivery system housing and coupled to the delivery system processor for automatically displaying to the user the data indicative of the physiological characteristic level of the user. Alternatively, the fluid delivery system may further include a display device contained in the delivery system housing and coupled to the delivery system processor for displaying data to the user, and a user interface contained in the housing and coupled to the delivery system processor for accepting one or more inputs from the user. At least one of the inputs may cause the display device to display the data indicative of the physiological characteristic level of the user received by the fluid delivery system. Also, the user interface may be dedicated for interfacing with the data indicative of the physiological characteristic level of the user received by the fluid delivery system.

In other particular embodiments, the fluid delivery system includes a memory contained in the delivery system housing for storing the data indicative of the physiological characteristic level of the user received by the fluid delivery system. Also, the fluid delivery system may include a display device contained in the housing and coupled to the delivery system processor for displaying to the user a historical trend or graph using the stored data indicative of the physiological characteristic level of the user received by the fluid delivery system.

In still other particular embodiments, the fluid delivery system may include a display device contained in the delivery system housing and coupled to the delivery system processor for displaying data to the user, and a user interface contained in the delivery system housing and coupled to the delivery system processor for accepting one or more inputs from the user. At least one of the inputs may cause the display device to display the most recent data indicative of the physiological characteristic level of the user received by the fluid delivery system. Also, at least a portion of the user interface may be dedicated for interfacing with the data indicative of the physiological characteristic level of the user received by the fluid delivery system.

In yet other particular embodiments, the fluid delivery system includes a display device contained in the delivery system housing and coupled to the delivery system processor for displaying data to the user, and a user interface contained in the delivery system housing and coupled to the delivery system processor for accepting one or more inputs from the user. At least one of the inputs causes the display device to display the data indicative of the physiological characteristic level of the user received by the fluid delivery system. Further, at least a portion of the user interface may be dedicated for interfacing with the data indicative of the physiological characteristic level of the user received by the fluid delivery system.

In still other embodiments, the fluid delivery system includes a user interface for accepting one or more inputs from the user, and the user interface is contained in the delivery system housing and coupled to the delivery system processor. At least one of the inputs programs the amount of the fluid infused into the user based upon the data indicative of the physiological characteristic level of the user received by the fluid delivery system. In yet other embodiments, the fluid delivery system includes a bolus estimator used in conjunction with the delivery system processor for estimating the amount of the fluid to be infused into the user based upon the data indicative of the physiological characteristic level of the user received by the fluid delivery system, an indication device coupled to the bolus estimator for indicating the estimated amount of fluid to be infused into the user, and a user interface for accepting one or more inputs from the user. At least one of the inputs accepts or modifies the estimated amount of the fluid to be infused into the user. In additional embodiments, the fluid delivery system includes a closed loop algorithm executed by the delivery system processor for automatically determining the amount of the fluid to be infused into the user based upon the data indicative of the physiological characteristic level of the user received by the fluid delivery system and causing the fluid delivery system to infuse the determined amount of the fluid into the user. In further embodiments, the fluid delivery system includes an indication device for indicating when the data indicative of the physiological characteristic level of the user received by the fluid delivery system is above or below a target characteristic value.

In still additional embodiments, the fluid delivery system includes a delivery system transmitter contained in the delivery system housing and coupled to the delivery system processor for transmitting one or more communications in the delivery system format. The relay device receiver further receives the communications from the fluid delivery system in the delivery system format, the relay device processor processes the communications from the fluid delivery system and converts the communications for transmission in the sensor system format, and the relay device transmitter transmits the converted communications in the sensor system format. Also, the sensor system further includes a sensor system receiver coupled to the sensor system processor for receiving the communications from the relay device in the sensor system format.

In still further embodiments, the fluid delivery system includes a display device contained in the delivery system housing and coupled to the delivery system processor for displaying data to the user, and a user interface contained in the delivery system housing and coupled to the delivery system processor for accepting one or more inputs from the user. At least one of the inputs generates a request for the data indicative of the physiological characteristic level of the user from the sensor system, at least one of the communications transmitted from the fluid delivery system through the relay device to the sensor system includes the request, and at least one of the communications including the data indicative of the physiological characteristic level of the user is transmitted from the sensor system through the relay device and received by the delivery system in response to the request. The display device then displays the data indicative of the physiological characteristic level of the user received by the fluid delivery system. Additionally, the user interface may be dedicated for interfacing from the fluid delivery system with the sensor system through the relay device. Also, the requested data is the most recent data indicative of the physiological characteristic level of the user received by the fluid delivery system.

In yet other embodiments, the data indicative of the physiological characteristic level of the user received by the fluid delivery system is uncalibrated data. The fluid delivery system includes a calibration algorithm executed by the delivery system processor for calibrating the uncalibrated data to generate one or more measurements indicative of the physiological characteristic level of the user.

In alternative embodiments, the data indicative of the physiological characteristic level of the user received by the fluid delivery system includes one or more calibrated measurements indicative of the physiological characteristic level of the user. In particular alternative embodiments, the sensor system includes a calibration algorithm executed by the sensor system processor for calibrating the signal indicative of the physiological characteristic level of the user to generate the one or more measurements indicative of the physiological characteristic level of the user, and the communications transmitted from the sensor system through the relay device and received by the fluid delivery system include the one or more measurements indicative of the physiological characteristic level of the user. In other particular alternative embodiments, the data indicative of the physiological characteristic level of the user received from the sensor system by the relay device is uncalibrated data. The relay device includes a calibration algorithm executed by the relay device processor for calibrating the uncalibrated data to generate one or more measurements indicative of the physiological characteristic level of the user, and the communications transmitted from the relay device and received by the fluid delivery system include the one or more measurements indicative of the physiological characteristic level of the user.

In additional alternative embodiments, at least one of the communications transmitted from the sensor system through the relay device and received by the delivery system includes one or more commands for programming the amount of the fluid infused into the user based upon the data indicative of the physiological characteristic level of the user. In some embodiments, the sensor system includes a display device coupled to the sensor system processor for displaying data to the user, and a user interface coupled to the sensor system processor for accepting one or more inputs from the user. At least one of the inputs causes the display device to display the data indicative of the physiological characteristic level of the user obtained by the sensor system. Also, at least another one of the inputs generates the one or more commands for programming the amount of the fluid infused into the user based upon the data indicative of the physiological characteristic level of the user obtained by the sensor system. In other embodiments, the sensor system includes a closed loop algorithm executed by the sensor system processor for automatically generating the one or more commands for programming the amount of the fluid to be infused into the user based upon the data indicative of the physiological characteristic level of the user obtained by the sensor system.

In further alternative embodiments, at least one of the communications transmitted from the sensor system to the relay device includes the data indicative of the physiological characteristic level of the user, and at least one of the communications transmitted from the relay device and received by the fluid delivery system includes one or more commands for programming the amount of the fluid infused into the user based upon the data indicative of the physiological characteristic level of the user. In particular embodiments, the relay device includes a display device coupled to the relay device processor for displaying data to the user, and a user interface coupled to the relay device processor for accepting one or more inputs from the user. At least one of the inputs causes the display device to display the data indicative of the physiological characteristic level of the user obtained by the sensor system. Also, at least another one of the inputs generates the one or more commands for programming the amount of the fluid infused into the user based upon the data indicative of the physiological characteristic level of the user obtained by the sensor system. In other particular embodiments, the relay device further includes a closed loop algorithm executed by the relay device processor for automatically generating the one or more commands for programming the amount of the fluid to be infused into the user based upon the data indicative of the physiological characteristic level of the user obtained by the sensor system.

In yet additional embodiments, the sensor system format and the delivery system format utilize different frequencies for communications transmitted from the sensor system through the relay device and received by the fluid delivery system. In some embodiments, the sensor system format and the delivery system format utilize different communication protocols for communications transmitted from the sensor system through the relay device and received by the fluid delivery system. The communication protocols may utilize different carrier media and/or information packaging for communications transmitted from the sensor system through the relay device and received by the fluid delivery system.

In particular embodiments, the delivery system processor has a unique identification code, and the sensor system processor has the capability to learn the unique identification code of the delivery system processor. Further, the communications transmitted from the sensor system through the relay device and received by the fluid delivery system include the unique identification code of the delivery system processor to substantially avoid interference with other devices. In other particular embodiments, the sensor system processor has a unique identification code, and the delivery system processor has the capability to learn the unique identification code of the sensor system processor. Further, the communications transmitted from the sensor system through the relay device and received by the fluid delivery system include the unique identification code of the sensor system processor to substantially avoid interference with other devices. In still other particular embodiments, the relay device processor has a unique identification code, and the sensor system processor has the capability to learn the unique identification code of the relay device processor. Also, the communications transmitted from the sensor system to the relay device include the unique identification code of the relay device processor to substantially avoid interference with other devices. In yet other particular embodiments, the relay device processor has a unique identification code, and the delivery system processor has the capability to learn the unique identification code of the relay device processor. Also, the communications transmitted from the relay device and received by the fluid delivery system include the unique identification code of the relay device processor to substantially avoid interference with other devices.

In additional embodiments, the relay device is coupled to the delivery system housing. In other embodiments, the relay device is contained in the delivery system housing. In still other embodiments, the relay device is coupled to the sensor system housing. In further embodiments, the sensor system is a glucose monitoring system, and the fluid delivery system is an insulin infusion device.

In another embodiment of the present invention, a relay device transfers information between a sensor system and a fluid delivery system. The sensor system measures a physiological characteristic level of a user, and the fluid delivery system infuses a fluid into the user. The relay device includes a sensor system receiver for receiving one or more communications from the sensor system in a sensor system format, a processor for processing the communications from the sensor system and converting the communications for transmission in a delivery system format, and a delivery system transmitter for transmitting the converted communications in the delivery system format to the fluid delivery system.

In some embodiments, the relay device includes a delivery system receiver for receiving one or more communications from the fluid delivery system in the delivery system format. The processor further processes the communications from the fluid delivery system and converts the communications for transmission in the sensor system format. The relay device also includes a sensor system transmitter for transmitting the converted communications in the sensor system format to the sensor system. In other embodiments, at least one of the communications transmitted from the sensor system through the relay device and received by the fluid delivery system include data indicative of the physiological characteristic level of the user. In yet other embodiments, at least one of the communications transmitted from the sensor system through the relay device and received by the fluid delivery system include one or more commands for programming an amount of the fluid to be infused into the user based upon data indicative of the physiological characteristic level of the user obtained by the sensor system.

In further embodiments, at least one of the communications transmitted from the sensor system to the relay device include data indicative of the physiological characteristic level of the user, and at least one of the communications transmitted from the relay device and received by the fluid delivery system include one or more commands for programming an amount of the fluid to be infused into the user based upon the data indicative of the physiological characteristic level of the user. Additionally, the relay device may include a display device coupled to the processor for displaying data to the user, and a user interface coupled to the processor for accepting one or more inputs from the user. At least one of the inputs causes the display device to display the data indicative of the physiological characteristic level of the user. Also, at least another one of the inputs generates the one or more commands for programming the amount of the fluid to be infused into the user based upon the data indicative of the physiological characteristic level of the user.

In still other embodiments, the sensor system format and the delivery system format utilize different frequencies for communications transmitted from the sensor system through the relay device to the fluid delivery system. In yet other embodiments, the sensor system format and the delivery system format utilize different communication protocols for communications transmitted from the sensor system through the relay device to the fluid delivery system. The communication protocols may utilize different carrier media and/or information packaging for communications transmitted from the sensor system through the relay device to the fluid delivery system.

In yet another embodiment of the present invention, a relay device transfers information between a sensor system and a fluid delivery system. The sensor system measures a physiological characteristic level of a user, and the fluid delivery system infuses a fluid into the user. The relay device includes a sensor system transceiver for transmitting and receiving one or more communications to and from the sensor system. The communications are transmitted and received in a sensor system format. The relay device also includes a delivery system transceiver for transmitting and receiving one or more communications to and from the fluid delivery system. The communications are transmitted and received in a delivery system format. The relay device further includes a processor for processing the communications from the sensor system and the fluid delivery system. The processor converts the communications received from the sensor system in the sensor system format for transmission in the delivery system format to the fluid delivery system, and further converts the communications received from the fluid delivery system in the delivery system format for transmission in the sensor system format to the sensor system.

In particular embodiments, at least one of the communications transmitted from the sensor system through the relay device and received by the fluid delivery system include data indicative of the physiological characteristic level of the user. In other particular embodiments, at least one of the communications transmitted from the sensor system through the relay device and received by the fluid delivery system include one or more commands for programming an amount of the fluid to be infused into the user based upon data indicative of the physiological characteristic level of the user obtained by the sensor system.

In additional embodiments, at least one of the communications transmitted from the sensor system to the relay device include data indicative of the physiological characteristic level of the user, and at least one of the communications transmitted from the relay device and received by the fluid delivery system include one or more commands for programming an amount of the fluid to be infused into the user based upon the data indicative of the physiological characteristic level of the user. Also, the relay device may include a display device coupled to the processor for displaying data to the user, and a user interface coupled to the processor for accepting one or more inputs from the user. At least one of the inputs causes the display device to display the data indicative of the physiological characteristic level of the user. Additionally, at least another one of the inputs generates the one or more commands for programming the amount of the fluid to be infused into the user based upon the data indicative of the physiological characteristic level of the user.

In further embodiments, the sensor system format and the delivery system format utilize different frequencies for communications transmitted between the sensor system and the fluid delivery system through the relay device. In additional embodiments, the sensor system format and the delivery system format utilize different communication protocols for communications transmitted between the sensor system and the fluid delivery system through the relay device. The communication protocols may utilize different carrier media and/or information packaging for communications transmitted between the sensor system and the fluid delivery system through the relay device.

In still another embodiment of the present invention, an infusion system for infusing a fluid into a user includes a sensor system and a fluid delivery system. The sensor system includes a sensor for producing a signal indicative of a physiological characteristic level of the user, a sensor system processor coupled to the sensor for processing the signal indicative of the physiological characteristic level of the user, and a sensor system transmitter coupled to the sensor system processor for transmitting one or more communications in a sensor system format. The fluid delivery system includes a delivery system housing, a relay device contained in the delivery system housing, a delivery system receiver, and a delivery system processor. The relay device includes a relay device receiver for receiving the communications from the sensor system in the sensor system format, a relay device processor for processing the communications from the sensor system and converting the communications for transmission in a delivery system format, and a relay device transmitter for transmitting the converted communications in the delivery system format. The delivery system receiver is contained in the delivery system housing and receives the communications from the relay device in the delivery system format. The delivery system processor is also contained in the delivery system housing and is coupled to the delivery system receiver, and processes the communications from the relay device in the delivery system format and controls an amount of the fluid infused into the user. The amount of the fluid infused into the user is determined based upon data indicative of the physiological characteristic level of the user obtained by the sensor system.

In particular embodiments, at least one of the communications transmitted from the sensor system through the relay device and received by the fluid delivery system include data indicative of the physiological characteristic level of the user. Additionally, the communications including the data indicative of the physiological characteristic level of the user may be automatically transmitted from the sensor system through the relay device and received by the fluid delivery system. Further, the fluid delivery system may also include a display device contained in the delivery system housing and coupled to the delivery system processor for automatically displaying to the user the data indicative of the physiological characteristic level of the user.

In other particular embodiments, the fluid delivery system includes a display device contained in the delivery system housing and coupled to the delivery system processor for displaying data to the user, and a user interface contained in the delivery system housing and coupled to the delivery system processor for accepting one or more inputs from the user. At least one of the inputs causes the display device to display the data indicative of the physiological characteristic level of the user received by the fluid delivery system.

In still other embodiments, the fluid delivery system includes a memory contained in the delivery system housing for storing the data indicative of the physiological characteristic level of the user received by the fluid delivery system. Additionally, the fluid delivery system may include a display device contained in the delivery system housing and coupled to the delivery system processor for displaying to the user a historical trend or graph using the stored data indicative of the physiological characteristic level of the user received by the fluid delivery system. Alternatively, the fluid delivery system may include a display device contained in the delivery system housing and coupled to the delivery system processor for displaying data to the user, and a user interface contained in the delivery system housing and coupled to the delivery system processor for accepting one or more inputs from the user. At least one of the inputs causes the display device to display the most recent data indicative of the physiological characteristic level of the user received by the fluid delivery system.

In additional embodiments, the fluid delivery system includes a display device contained in the delivery system housing and coupled to the delivery system processor for displaying data to the user, and a user interface contained in the delivery system housing and coupled to the delivery system processor for accepting one or more inputs from the user. At least one of the inputs causes the display device to display the data indicative of the physiological characteristic level of the user received by the fluid delivery system. In further embodiments, the fluid delivery system includes a user interface contained in the delivery system housing and coupled to the delivery system processor for accepting one or more inputs from the user. At least one of the inputs programs the amount of the fluid infused into the user based upon the data indicative of the physiological characteristic level of the user received by the fluid delivery system.

In yet other embodiments, the fluid delivery system includes a bolus estimator used in conjunction with the delivery system processor for estimating the amount of the fluid to be infused into the user based upon the data indicative of the physiological characteristic level of the user received by the fluid delivery system, an indication device coupled to the bolus estimator for indicating the estimated amount of fluid to be infused into the user, and a user interface for accepting one or more inputs from the user. At least one of the inputs accepts or modifies the estimated amount of the fluid to be infused into the user. In still further embodiments, the fluid delivery system includes a closed loop algorithm executed by the delivery system processor for automatically determining the amount of the fluid to be infused into the user based upon the data indicative of the physiological characteristic level of the user received by the fluid delivery system and causing the fluid delivery system to infuse the determined amount of the fluid into the user. In still additional embodiments, the fluid delivery system includes an indication device for indicating when the data indicative of the physiological characteristic level of the user received by the fluid delivery system is above or below a target characteristic value. In even additional embodiments, the data indicative of the physiological characteristic level of the user received by the fluid delivery system is uncalibrated data, and the fluid delivery system further includes a calibration algorithm executed by the delivery system processor for calibrating the uncalibrated data to generate one or more measurements indicative of the physiological characteristic level of the user.

In some embodiments, the sensor system format and the delivery system format utilize different frequencies for communications transmitted from the sensor system through the relay device and received by the fluid delivery system. In other embodiments, the sensor system format and the delivery system format utilize different communication protocols for communications transmitted from the sensor system through the relay device and received by the fluid delivery system. The different communication protocols may utilize different carrier media and/or information packaging for communications transmitted from the sensor system through the relay device and received by the fluid delivery system.

In yet further embodiments, the delivery system processor has a unique identification code, and the sensor system processor has the capability to learn the unique identification code of the delivery system processor. The communications transmitted from the sensor system through the relay device and received by the fluid delivery system include the unique identification code of the delivery system processor to substantially avoid interference with other devices. In yet additional embodiments, the sensor system processor has a unique identification code, and the delivery system processor has the capability to learn the unique identification code of the sensor system processor. The communications transmitted from the sensor system through the relay device and received by the fluid delivery system include the unique identification code of the sensor system processor to substantially avoid interference with other devices. Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

FIG. 2(a)-2(c) are perspective views of a blood glucose monitoring system in accordance with embodiments of the present invention.

FIGS. 8(a)-8(c) are perspective views of a relay device placed on an infusion pump in accordance with embodiments of the present invention.

FIGS. 9(a)-9(e) are block diagrams of a relay device in accordance with embodiments of the present invention.

DETAILED DESCRIPTION OF THE PREFERRED EMBODIMENTS

Figure 1:
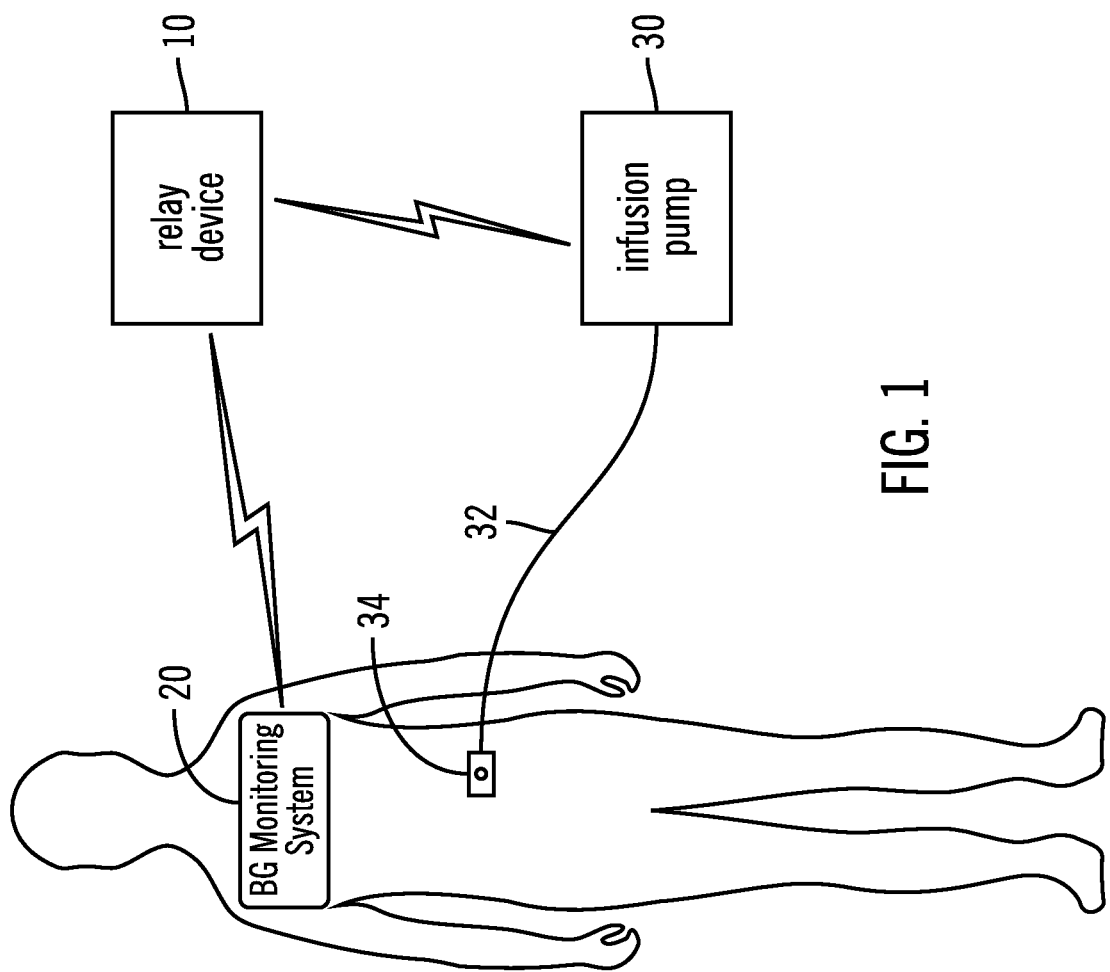
FIG. 1 is a block diagram of a system for transferring information between a blood glucose monitoring system and an infusion pump through a relay device in accordance with an embodiment of the present invention.

As shown in the drawings for purposes of illustration, the invention is embodied in a relay device for transferring information between a sensor system for measuring a physiological characteristic level of a user's body and a fluid delivery system for delivering fluid into the user's body. The relay device receives information from one system in a first format, converts the information into a second format appropriate for the other system, and then transmits the converted information to the other system. Therefore, the relay device enables communication between the sensor system and the fluid delivery system, even if the systems are not developed in conjunction with one another. For example, sensor data or measurements may be communicated from the sensor system via the relay device to the fluid delivery system, and then utilized to adjust the amount of fluid delivered by the fluid delivery system into the user's body. Thus, the relay device encourages the user or caregiver to utilize the sensor data or measurements in order to adjust the amount of fluid delivered into the user's body by the fluid delivery system. Further, the sensor measurements may be displayed on the fluid delivery system for the user or caregiver to see. Therefore, the relay device allows the user or caregiver to interface with the sensor system (e.g., view the sensor measurements) utilizing a single device, the fluid delivery system. Particular embodiments are directed toward use of ambulatory sensor and fluid delivery systems that are programmed and adjusted primarily by the user or a caregiver, such as the user's parent. Other embodiments are directed toward use of hospital-based sensor and fluid delivery systems that are programmed and adjusted primarily by a caregiver, such as the user's physician or nurse.

In preferred embodiments, the sensor system is a blood glucose (BG) monitoring system, which utilizes a sensor placed in a user to automatically measure the user's BG level, either periodically or continuously. In particular embodiments, the sensor may measure additional physiological characteristic levels of the user, such as blood oxygen, temperature, and the like. The sensor may be implanted in and/or through subcutaneous, dermal, sub-dermal, inter-peritoneal, or peritoneal tissue, and may be a sensor in contact with the user's body fluid, such as the user's blood, interstitial fluid, and the like. In preferred embodiments, the fluid delivery system is an insulin delivery device, such as an external insulin infusion pump, which regulates the amount of insulin delivered into the user's body. The relay device receives information from one system in a first format, converts the information into a second format appropriate for the other system, and then transmits the converted information to the other system. For example, the relay device may receive BG data or measurements from the BG monitoring system in a sensor system format (e.g., at a frequency of 131 kilohertz, utilizing radio frequency (RF) carrier media, in packets of 107 bytes), convert such data or measurements into a delivery system format appropriate for the insulin infusion pump (e.g., to a frequency of 916 megahertz, utilizing infrared (IR) carrier media, in packets of 71 bytes), and then transmit such converted data or measurements to the insulin infusion pump. The amount of insulin delivered into the user's body by the infusion pump may then be adjusted, either manually by the user or a caregiver or automatically, in response to the received BG data or measurements. In some embodiments, the BG measurements may also be displayed on the insulin infusion pump.

However, in alternative embodiments of the present invention, the sensor system may include other types of sensors, such as optical, enzymatic, fluorescent, or the like. In additional alternative embodiments, the sensor system may measure the user's BG level only when requested by the user, or a BG meter may be utilized to measure the user's BG level based on a sampling of the user's blood. In further alternative embodiments, the sensor system may measure other physiological characteristic levels of the user, such as heart rate, blood oxygen, pH, peroxide, respiratory rate, body temperature, blood pressure, perspiration, brain wave activity, cholesterol level, ketone level, medication concentration, viral load (e.g., HIV), and the like. The sensor system may also include multiple sensors—one or more sensors to measure the user's BG level and one or more sensors to measure such other physiological characteristic levels of the user. In other alternative embodiments, the sensor system may measure the physiological characteristic levels of the user from body fluids other than blood, such as interstitial fluid, spinal fluid, saliva, urine, tears, sweat, or the like. In still other alternative embodiments, the fluid delivery system may be an implantable infusion pump, an infusion pump that uses a combination of implantable and external components, a pen injector, a disposable pump, an intra venous drip system, or the like. In yet other alternative embodiments, the fluid delivery system may deliver fluids other than insulin, including peptides, proteins, sugars, vitamins, antigens, hormones, steroids, medicaments, drugs, pain killers, anti-cancer agents, anti-coagulants, stimulants, tranquilizers, sedatives, and the like. Particular embodiments are directed towards use in humans; however, alternative embodiments may be used in animals.

In preferred embodiments of the present invention, a relay device transfers information between a sensor system for measuring a physiological characteristic level of a user's body and a fluid delivery system for delivering fluid into the user's body. In the embodiment illustrated in FIG. 1, the sensor system is a BG monitoring system 20, which utilizes a sensor that is placed in a user to measure the user's BG level. The sensor may measure additional physiological characteristic levels of the user, such as blood oxygen, temperature, or the like.

In particular embodiments, the BG monitoring system 20 is an implantable glucose monitoring system, and is generally of the type described in U.S. Pat. No. 6,368,274, and disclosed in U.S. patent application Ser. No. 10/034,740, filed Dec. 27, 2001 and entitled "Implantable Sensor Flush Sleeve," and U.S. Provisional Patent Application filed Sep. 27, 2002 and entitled "Implantable Sensor Method and System," which are herein incorporated by reference. Referring to FIG. 2(*a*), the BG monitoring system 20 includes a glucose sensor set 50 and a glucose monitor 54. The sensor set 50 and glucose monitor 54 are implanted in the user's sub-dermal or inter-peritoneal tissue, and are in contact with the user's blood or other body fluid, to measure the user's BG level. For example, the sensor set 50 may be implanted into the central vein of the user's heart, and the glucose monitor 54 may be located in the user's chest cavity. Alternatively, the sensor set 50 may be placed in the user's peritoneum, and the glucose monitor 54 may be located in the user's abdominal cavity. The glucose monitor 54 includes a processor (not shown) for processing data as it is received from the sensor set 50, and a transmitter and/or receiver (not shown) for transferring the data to and/or from a data processor, such as a dedicated processor 56 designed specifically to work with the glucose monitor 54, a computer, communication station, or the like. The data processor 56 preferably comprises a relatively compact, portable housing that may be easily worn on clothing or jewelry, placed in a pocket, concealed under clothing, or the like. However, the BG monitoring system 20 may also be included in a hospital-based system, and the data processor 56 may comprise a housing that may be included in a monitor, placed on an intravenous (IV) pole, or the like near the patient's bed.

Figure 11:
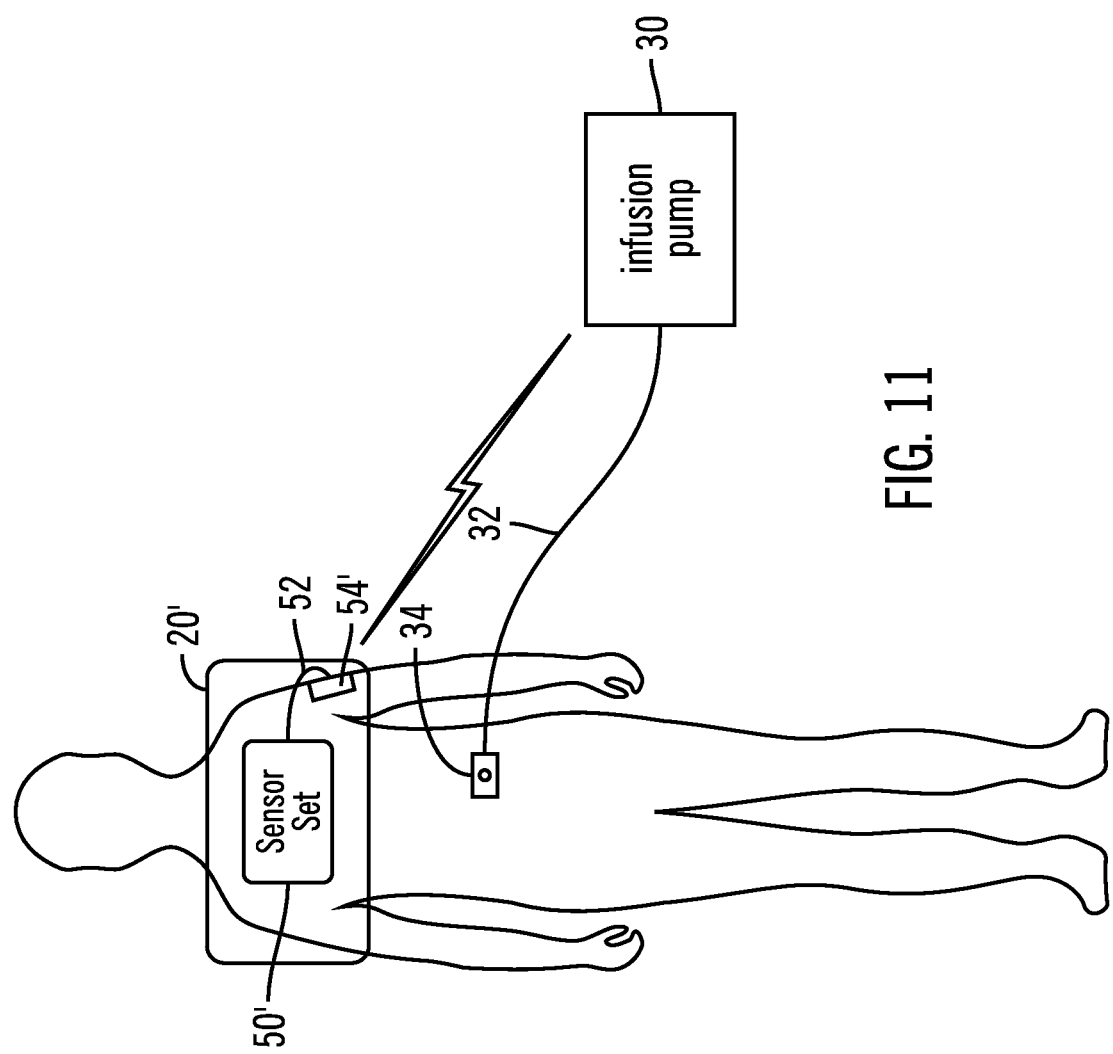
FIG. 11 is a block diagram of a system for transferring information between a blood glucose monitoring system and an infusion pump using a relay device incorporated into the infusion pump in accordance with yet another embodiment of the present invention.

In other particular embodiments, the BG monitoring system 20 is a telemetered glucose monitoring system, and may generally be of the type described in U.S. patent application Ser. No. 09/377,472, filed Aug. 19, 1999 and entitled "Telemetered Characteristic Monitor System and Method of Using the Same," which is herein incorporated by reference. The BG monitoring system 20 may also be a vascular glucose monitoring system, and may generally be of the type described in U.S. patent application Ser. No. 10/036,93, filed Dec. 28, 2001 and entitled "Sensing Apparatus and Process," and U.S. Provisional Patent Application filed Sep. 27, 2002 and entitled "Multilumen Catheter," which are herein incorporated by reference. Referring to FIG. 2(*b*), the BG monitoring system 20' may include a glucose sensor set 50' and a glucose monitor 54'. The sensor set 50' includes a glucose sensor that is placed in and/or through the user's subcutaneous, dermal, sub-dermal, inter-peritoneal, peritoneal, muscle, lymph, or organ tissue, veins, arteries, or the like, and may be in contact with the user's blood or other body fluid, to measure the user's BG level. The sensor set 50' is connected to the glucose monitor 54' via a cable 52, and the glucose monitor 54' includes a processor (not shown) for processing data as it is received from the sensor set 50' via the cable 52. For example, the sensor set 50' may be placed in the user's subcutaneous tissue, and the glucose monitor 54' may be adhered to the user's body. Alternatively, the sensor set 50' may be inserted into one lumen of a multilumen catheter, which may then be implanted in the central vein of the user's heart and include an extension lead for connecting to the glucose monitor 54' via the cable 52, and the glucose monitor 54' may be adhered to the user's body, as shown in FIG. 11. The other lumen(s) of the multilumen catheter may be utilized for sampling other physiological characteristic levels of the user and/or delivering fluids into the user's body, such as protein nutrition, blood products, medication, lipids, and the like. Such a multilumen catheter may generally be of the type described in U.S. Provisional Patent Application filed Sep. 27, 2002 and entitled "Multilumen Catheter," which is herein incorporated by reference.

The glucose monitor 54' may also include a transmitter and/or receiver (not shown) for transferring the data to and/or from a data processor, such as a dedicated processor 56' designed specifically to work with the glucose monitor 54', a computer, communication station, or the like. The data processor 56' preferably comprises a relatively compact, portable housing that may be easily worn on clothing or jewelry, placed in a pocket, concealed under clothing, or the like. However, the BG monitoring system 20 may also be included in a hospital-based system, and the data processor 56' may comprise a housing that may be included in a monitor, placed on an intravenous (IV) pole, or the like near the patient's bed. In alternative embodiments, the cable 52 may be omitted, and the sensor set 50' may be directly connected to the glucose monitor 54'.

In yet other particular embodiments, the BG monitoring system 20 may be a continuous glucose monitoring system, and may generally be of the type described in U.S. Pat. No. 6,424,847, which is herein incorporated by reference. Referring to FIG. 2(*c*), the BG monitoring system 20" may include a glucose sensor set 50" and a glucose monitor 54". The sensor set 50" includes a glucose sensor that is placed in and/or through the user's subcutaneous, dermal, sub-dermal, inter-peritoneal, peritoneal, muscle, lymph, or organ tissue, veins, arteries, or the like, and may be in contact with the user's blood or other body fluid, to measure the user's BG level. The sensor set 50" is connected to the glucose monitor 54" via a cable 52', and the glucose monitor 54" includes a processor (not shown) for processing data as it is received from the sensor set 50" via the cable 52'. The glucose monitor 54" comprises a relatively compact, portable housing that may be easily worn on clothing or jewelry, placed in a pocket, concealed under clothing, or the like. However, the BG monitoring system 20 may also be included in a hospital-based system, and the glucose monitor 54" may comprise a housing that may be included in a monitor, placed on an intravenous (IV) pole, or the like near the patient's bed. The glucose monitor 54" may also include a transmitter and/or receiver (not shown) for transferring the data to and/or from a data processor (not shown), such as a computer, communication station, or the like. In alternative embodiments, the cable 52' may be omitted, and the sensor set 50" may be directly connected to the glucose monitor 54".

In alternative embodiments, the BG monitoring system 20 may include other types of sensors, such as optical, enzymatic, fluorescent, or the like. In further alternative embodiments, the sensor system may measure other physiological characteristic levels of the user, such as heart rate, blood oxygen, pH, peroxide, respiratory rate, body temperature, blood pressure, perspiration, brain wave activity, cholesterol level, ketone level, medication concentration, viral load (e.g., HIV), and the like. The sensor system may also include multiple sensors—one or more sensors to measure the user's BG level and one or more sensors to measure such other physiological characteristic levels of the user. For example, the BG monitoring system 20 may include a glucose sensor set 50 inserted in or on the user's body to measure the user's BG level and an oxygen sensor to measure the oxygen level at or near the insertion site of the sensor set 50. The measured oxygen level may then be used to determine the effectiveness of the sensor set 50, the formation of foreign bodies near the sensor set 50, or the like. In other alternative embodiments, the sensor system may measure the physiological characteristic levels of the user from body fluids other than blood, such as interstitial fluid, spinal fluid, saliva, urine, tears, sweat, or the like.

In particular embodiments, the BG monitoring system 20 automatically measures the user's BG level on a periodic basis. In other particular embodiments, the BG monitoring system 20 automatically measures the user's BG level on a continuous basis. In alternative embodiments, the BG monitoring system 20 may not automatically measure the user's BG level. For example, the BG monitoring system 20 may include a user interface, such as a keypad 60, which may be utilized by the user to request a BG measurement from the BG monitoring system 20. Alternatively, the BG monitoring system 20 may include a BG meter, which measures the user's BG level based on a sampling of the user's blood.

In preferred embodiments, the BG monitoring system 20 includes a transmitter and/or receiver (not shown) for communicating with external devices, such as a remote programmer (not shown) for the BG monitoring system 20, a BG meter (not shown), the relay device 10, the infusion pump 30 via the relay device 10, or the like. For example, the glucose monitor 54 and/or data processor 56 may include the transmitter and/or receiver. The BG monitoring system 20 preferably communicates with such external devices using radio frequency (RF) communication. Alternatively, other modes of communication may be utilized, such as infrared (IR), wired, ultrasonic, optical, or the like.

In particular embodiments, the BG monitoring system 20 may also include a display and a user interface. Referring to FIGS. 2(*a*)-2(*b*), the data processor 56 includes a display 58 and a keypad 60 with one or more keys. The glucose monitor 54 utilizes the transmitter and/or receiver (not shown) to transfer data to and/or from the data processor 56. Alternatively, referring to FIG. 2(*c*), the glucose monitor 54" may include the display 58" and keypad 60" with one or more keys. The user may utilize the display 58 and/or keypad 60 to display the user's current BG level, view other BG information recorded or calculated by the glucose monitor 54 and/or data processor 56 (e.g., average BG level, BG trends, graphs of historical BG measurements), view alarms or other messages, program the BG monitoring system 20, enter calibration or other data into the BG monitoring system 20, download information from the BG monitoring system 20, and the like. In particular embodiments, the user may also utilize the display 58 and/or keypad 60 to transmit data, delivery commands, and/or other information to the infusion pump 30 via the relay device 10. In alternative embodiments, the user interface may include one or more buttons, switches, levers, joystick, roller ball, mouse, keyboard, and the like. In further alternative embodiments, the keypad 60 may be omitted, and the display 58 may be used as a touch screen input device. In other alternative embodiments, the display and/or user interface may be omitted from the BG monitoring system 20, and instead included on the relay device 10 and/or infusion pump 30.

In preferred embodiments, the BG monitoring system 20 stores information in a memory (not shown) of the BG monitoring system 20 for subsequent review and/or downloading to a storage media. Information stored by the BG monitoring system 20 may include one or more of raw BG data, calibrated BG measurements, time stamps, sensor alarms, sensor settings, calibration data, sensor performance data, sensor errors, sensor system diagnostics, statistics, user information, serial number, and the like. In preferred embodiments, information is transmitted from the BG monitoring system 20 to the infusion pump 30 via the relay device 10, and then downloaded to a storage media from the infusion pump 30. The storage media may include one or more of a personal computer (PC), a central server, an electronic memory, a personal digital assistant (PDA), a cell phone, a laptop computer, magnetic memory, silicon memory, a data storage device, and the like. In alternative embodiments, information may be downloaded to the storage media directly from the BG monitoring system 20 through an interface, such as a transmitter, a cable, a communication station, or the like. In particular alternative embodiments, information may be downloaded from the data processor 56 to the storage media. In other alternative embodiments, information may be downloaded from the glucose monitor 54 to the storage media. In further alternative embodiments, information may be transmitted from the BG monitoring system 20 to the relay device 10, and then downloaded to the storage media from the relay device 10. In other alternative embodiments, information may be downloaded to the storage media from more than one of the BG monitoring system 20, relay device 10, and infusion pump 30.

In preferred embodiments, sensor calibration data is provided to the BG monitoring system 20 by communication with an external device, such as a BG meter or other BG measuring device (not shown). The BG monitoring system 20 preferably includes a transmitter and/or receiver (not shown) for communicating with such external devices. For example, the glucose monitor 54 and/or the data processor 56 may include the transmitter and/or receiver. The user obtains a BG reference reading utilizing a BG meter or other BG measuring device, which then transmits the BG reference reading to the BG monitoring system 20, either directly or via the relay device 10. In alternative embodiments, the user may manually enter sensor calibration data into the BG monitoring system 20. In particular alternative embodiments, the user may utilize the display 58 and/or user interface 60 on the data processor 56, as shown in FIGS. 2(*a*)-2(*b*), to manually input the calibration data into the BG monitoring system 20. In other particular alternative embodiments, the user may utilize the display 58" and/or user interface 60" on the glucose monitor 54", as shown in FIG. 2(*c*), to manually input the calibration data into the BG monitoring system 20.

In the embodiment illustrated in FIGS. 1 and 3(*a*)-3(*b*), the fluid delivery system is an external infusion pump 30, which regulates the flow of fluid, preferably medication such as insulin, through flexible tubing 32 and into an infusion set 34 or the like that is adhered to the user's body. Infusion sets 34 that may be used are described in, but not limited to, U.S. Pat. Nos. 4,723,947; 4,755,173; 5,176,662; 5,584,813; and 6,056,718, which are herein incorporated by reference. The infusion pump 30 is generally of the type described in U.S. Pat. Nos. 4,562,751; 4,685,903; 5,080,653; 5,097,122; 5,505,709; and 6,248,093; and disclosed in U.S. patent application Ser. No. 09/334,858, filed Jun. 16, 1999 and entitled "External Infusion Device with Remote Programming, Bolus Estimator and/or Vibration Alarm Capabilities," which are herein incorporated by reference. In alternative embodiments, the fluid delivery system may be an implantable infusion pump, an infusion pump that uses a combination of implantable and external components, a pen injector, disposable pump, an intra venous drip system, or the like. In still other alternative embodiments, the fluid delivery system may deliver fluids other than insulin, including peptides, proteins, sugars, vitamins, antigens, hormones, steroids, medicaments, drugs, pain killers, anti-cancer agents, anti-coagulants, stimulants, tranquilizers, sedatives, and the like.

Referring to FIGS. 3(*a*)-3(*b*), the infusion pump 30 comprises a relatively compact, portable housing that may be easily worn on clothing or jewelry, placed in a pocket, concealed under clothing, or the like. However, the infusion pump 30 may also be included in a hospital-based system, and the infusion pump 30 may comprise a housing that may be included in a monitor, placed on an intravenous (IV) pole, or the like near the patient's bed. The infusion pump 30 preferably includes a processor 150 for running programs and controlling the infusion pump 30. The processor 150 is coupled to an internal memory device 154 that stores programs, history data, user defined information and parameters. In preferred embodiments, the memory device 154 is a ROM and DRAM; however, in alternative embodiments, the memory device 154 may include other memory storage devices, such as RAM, EPROM, dynamic storage such as flash memory, energy efficient hard-drive, or the like. The processor 150 is also coupled to a drive mechanism 160 that is connected to a fluid reservoir 162 containing fluid that is delivered through the tubing 32 and into the infusion set 34 adhered to the user's body. The processor 150 may additionally be coupled to a bolus estimator 164, which estimates an appropriate amount of insulin to be delivered to the user based on the user's BG level, the amount of carbohydrates to be consumed, and the like. The bolus estimator 164 may generally be of the type described in U.S. patent application Ser. No. 09/334,858, filed Jun. 16, 1999 and entitled "External Infusion Device with Remote Programming, Bolus Estimator and/or Vibration Alarm Capabilities," which is herein incorporated by reference.

The infusion pump 30 further includes a communication system 152 coupled to the processor 150 for communicating with external devices, such as a remote programmer (not shown) for the infusion pump 30, the BG monitoring system 20 via the relay device 10, the relay device 10, or the like. The communication system 152 may include a transmitter and/or receiver (not shown) for communicating with such external devices. The infusion pump 30 preferably communicates with such external devices using radio frequency (RF) communication. Alternatively, other modes of communication may be utilized, such as infrared (IR), wired, ultrasonic, optical, or the like.

In some embodiments, the transmitter and/or receiver (not shown) of the communication system 152 may be capable of communicating with certain external devices utilizing a particular frequency and/or communication protocol, such as the remote programmer (not shown) for the infusion pump 30 or the like. The infusion pump 30 may include another transmitter and/or receiver (not shown) as part of the relay device 10 incorporated in the infusion pump 30 itself (as shown and described below in the embodiment of FIGS. 8(d) and 10-12), which is capable of communicating with other external devices utilizing another particular frequency and/or communication protocol, such as the BG monitoring system 20 or the like. In other embodiments, the transmitter and/or receiver (not shown) of the communication system 152 may be capable of communicating with various external devices utilizing different frequencies and/or communication protocols.

The infusion pump 30 also includes a display 100 and/or a user interface 110. In preferred embodiments, the display 100 is a monochromatic liquid crystal display (LCD). In alternative embodiments, the display 100 is a light emitting diode (LED) display, a cathode ray tube (CRT) display, a touch screen, a color LCD, or the like.

In preferred embodiments, the user interface is a keypad 110 including one or more keys with selectable functions. The infusion pump 30 is preferably programmed through the keypad 110, or alternatively, by commands received from an external device, such as a remote programmer, the BG monitoring system 20 via the relay device 10, the relay device 10, or the like. The keypad 110 may generally be of the type, and operate in a manner similar to that, disclosed in U.S. patent application Ser. No. 09/334,858, filed Jun. 16, 1999 and entitled "External Infusion Device with Remote Programming, Bolus Estimator and/or Vibration Alarm Capabilities," and Ser. No. 09/784,949, filed Feb. 15, 2001 and entitled "Improved Infusion Device Menu Structure and Method of Using the Same," which are herein incorporated by reference.

In the illustrated embodiment, the keypad 110 includes an Up-Arrow key 112, a Down-Arrow key 114, an ACT (activate) key 116, an ESC (escape) key 118, and an Express Bolus key 120 for programming the infusion pump 30. The keypad 110 also includes a dedicated key 122 for interfacing with the BG monitoring system 20 via the relay device 10. In particular embodiments, the user chooses a function and then selects which key will perform that function. For example, while the display 100 is blank, the user may select the Express Bolus key 120 to quickly set a bolus amount, or the ESC key 118 to show a status information screen on the display 100. In other particular embodiments, the user selects one or more keystrokes to perform a function. For example, while the display 100 is blank, the user may first select the ACT key 116 to show a main menu screen, then the Up-Arrow and Down-Arrow keys 112 and 114 to scroll through the menu choices, and then the ACT key 116 again to select a menu option. The user selects the keys 112, 114, 116, 118, 120, and/or 122 on the keypad 110 to perform functions on the infusion pump 30, such as starting or stopping a bolus or basal delivery, accessing historical data or status information, setting a utility (e.g., date, time, serial number, or the like), turning on or off a feature (e.g., light, key lock, temporary operation, or the like), escaping to a home display screen, backing up to a previous screen, deleting or approving an input, scrolling, priming, resetting, and the like. In particular embodiments, the display 100 and/or user interface 110 may also be utilized to input information into and/or display information from the BG monitoring system 20 via the relay device 10, such as viewing sensor measurements received from the BG monitoring system 20 on the display 100 of the infusion pump 30. In alternative embodiments, the keypad 110 may include more or less keys, or have different key arrangements than those illustrated in the figures.

In further alternative embodiments, one or more keys on the keypad 110 may be programmable. In particular embodiments, the user may define one or more keystrokes to cause the infusion pump 30 to perform one or more functions. For example, a first user may define key 120 on a first infusion pump 30 to cause the display 100 to show the most recent sensor measurement, while a second user may define key 120 on a second infusion pump 30 to perform an express bolus function. In other alternative embodiments, the user interface may include one or more buttons, switches, levers, joysticks, roller balls, mice, keyboards, and the like. In still other alternative embodiments, the keypad 110 may be omitted, and the display 100 may be used as a touch screen input device.

The infusion pump 30 may provide feedback to the user on status or programming changes visibly on the display 100 and/or through lights (not shown) on the infusion pump 30, audibly through a speaker 156, and/or tactilely through a vibrator 158. The infusion pump 30 may also provide the user with a visible alarm via the display 100 and/or lights, an audible alarm via the speaker 156, and/or a vibration alarm via the vibrator 158, such as a warning that is indicative of a low reservoir or low battery, an alarm or warning that is indicative of a sensor measurement received from the BG monitoring system 20 via the relay device 10 that is above or below target glycemic values, or the like. In alternative embodiments, the display 100, keypad 110, lights, speaker 156, and/or vibrator 158 may be omitted from the infusion pump 30, and instead, included on the relay device 10 and/or the BG monitoring system 20. In further alternative embodiments, the display 100, keypad 110, lights, speaker 156, and/or vibrator 158 may be omitted, the infusion pump 30 may be implanted in the user's body, and all programming may be handled through a communication system using wireless modes of communication, such as radio frequency (RF), infrared (IR), and the like.

In preferred embodiments, the infusion pump 30 stores information in a memory (not shown) of the infusion pump 30 for subsequent review and/or downloading to a storage media. Information stored by the infusion pump 30 includes one or more of insulin delivery rates, insulin bolus amounts, time stamps, alarms, errors, warnings, utility settings, statistics, profiles, user information, serial number, commands, force measurements, pressure measurements, and the like. In preferred embodiments, information is downloaded directly from the infusion pump 30 to a storage media through an interface, such as a transmitter, cable, communication station, or the like. In particular embodiments, an external communication link (not shown) may be connected via a cable to a serial, USB, or the like port of a computer. The infusion pump 30 may include an RF transmitter or transceiver (not shown), which transmits information to an RF receiver or transceiver in the external communication link for downloading to the computer. In other particular embodiments, information may be downloaded from the infusion pump 30 through a communication station generally of the type disclosed in U.S. Pat. No. 5,376,070, which is herein incorporated by reference. In still other particular embodiments, information may be downloaded from the infusion pump 30 through a BG meter (not shown) as disclosed in U.S. Provisional Patent Application Ser. No. 60/412,998, filed Sep. 23, 2002 and entitled "System for Providing Blood Glucose Measurements to Bolus Estimator," which is herein incorporated by reference. The storage media may include one or more of a personal computer (PC), a central server, an electronic memory, a personal digital assistant (PDA), a cell phone, a laptop computer, magnetic memory, silicon memory, a data storage device, and the like. In alternative embodiments, information may be transmitted from the infusion pump 30 to the BG monitoring system 20 via the relay device 10, and then downloaded to a storage media from the BG monitoring system 20. In further alternative embodiments, information may be transmitted from the infusion pump 30 to the relay device 10, and then downloaded to the storage media from the relay device 10. In other alternative embodiments, information may be downloaded to the storage media from more than one of the BG monitoring system 20, relay device 10, and infusion pump 30.

In the embodiment illustrated in FIG. 1, the relay device 10 transfers information between the BG monitoring system 20 and the infusion pump 30. In preferred embodiments, the relay device 10 comprises a relatively compact, portable housing 200 without a user interface or a display, as illustrated in FIG. 6(*a*). The relay device 10 may be easily worn on clothing or jewelry, placed in a pocket, concealed under clothing, or the like. In alternative embodiments, the relay device 10' may include a housing 200' with a single key 202, as shown in FIG. 6(*b*). The single key 202 provides a user interface for the user to request new information from the BG monitoring system 20.

In further alternative embodiments, the relay device 10" may include a housing 200" with a keypad 204, as shown in FIG. 6(*c*). The keypad 204 may include more than one key, and at least one of the keys may be utilized by the user to send data or commands to the infusion pump 30. In the illustrated embodiment, the keypad 204 includes an Up-Arrow key 206, a Down-Arrow key 208, and an ACT (activate) key 210 for programming the infusion pump 30 from the relay device 10 in a manner similar to that shown and described in the embodiment of FIG. 3(*a*). The keypad 204 also includes a dedicated key 212 for interfacing with and requesting data from the BG monitoring system 20. However, in alternative embodiments, the keypad 204 may include more or less keys or different key arrangements than those illustrated in FIG. 6(*c*).

In other alternative embodiments, the relay device 10''' may include a housing 200''' with a display 214 and a keypad 216, as shown in FIG. 6(*d*). In particular alternative embodiments, the display 214 may be a monochromatic liquid crystal display (LCD). In other particular alternative embodiments, the display 214 may be a light emitting diode (LED) display, a cathode ray tube (CRT) display, a touch screen, a color LCD, or the like. The keypad 216 may include more than one key, and at least one of the keys may be utilized by the user to send data or commands to the infusion pump 30. In the illustrated embodiment, the keypad 216 includes an Up-Arrow key 218, a Down-Arrow key 220, an ACT (activate) key 222, and an ESC (escape) key 224 for programming the infusion pump 30 from the relay device 10 in a manner similar to that shown and described in the embodiment of FIG. 3(*a*). The keypad 216 also includes a dedicated key 226 for interfacing with and requesting data from the BG monitoring system 20. However, in alternative embodiments, the keypad 216 may include more or less keys or different key arrangements than those illustrated in FIG. 6(*d*). In still other alternative embodiments, the relay device 10 may be a computer system (not shown), such as a personal computer (PC), a personal digital assistant (PDA), a central data system (such as is used in hospitals to store or track data, Internet systems, or the like), or the like.

Figure 7A:
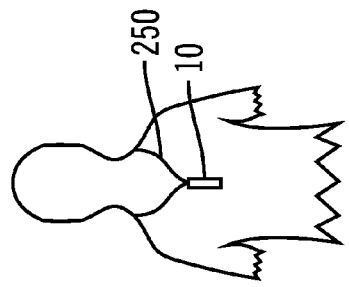
FIGS. 7(a)-7(c) are perspective views of a relay device placed on a body of a user in accordance with embodiments of the present invention.
Figure 7B:
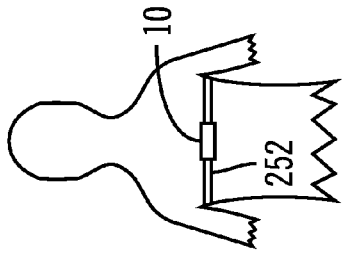
Figure 7C:
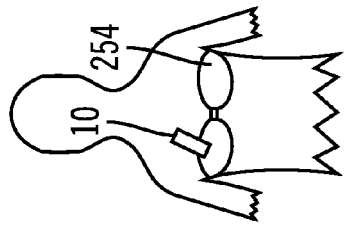

In preferred embodiments, the relay device 10 is positioned on the user's body near the BG monitoring system 20. For example, the relay device 10 may be positioned on the user's body using a necklace 250 to hold the relay device 10 like a pendant (as shown in FIG. 7(*a*)), using a belt or strap 252 to hold the relay device 10 in place (as shown in FIG. 7(*b*)), or by placing the relay device 10 in a clothing garment 254 or clipping the relay device 10 in place (as shown in FIG. 7(*c*)). Positioning the relay device 10 near the BG monitoring system 20 is especially useful to minimize the power required by the transmitter and/or receiver in the BG monitoring system 20 to send and/or receive signals between the BG monitoring system 20 and the relay device 10. Other methods may be used to locate the relay device 10 near the BG monitoring system 20, such as using tape or adhesive to hold the relay device 10 in place, holding the relay device 10 in a hand and bringing the hand near the BG monitoring system 20, or the like.

In alternative embodiments, the relay device 10 may be incorporated with the infusion pump 30 to minimize the number of components that the user must handle. For example, the relay device 10 may be incorporated into a clip that is attached to the infusion pump 30 to hold the infusion pump 30 in place on the user's body, as shown in FIG. 8(*a*). Alternatively, the relay device 10' may be mounted on a side of the infusion pump 30, as shown in FIG. 8(*b*). Additionally, the relay device 10" may be attached to a bottom of the infusion pump 30, as shown in FIG. 8(*c*). In other alternative embodiments, the relay device 10 may be incorporated with the BG monitoring system 20 in a manner similar to that shown and described in the embodiments of FIGS. 8(*a*)-8(*c*). For example, the relay device 10 may be incorporated into a clip that is attached to, or mounted on a side of, or attached to a bottom of, the data processor 56 shown in FIGS. 2(*a*)-2(*b*) or the glucose monitor 54" shown in FIG. 2(*c*).

In further alternative embodiments, the relay device 10 may be incorporated into the infusion pump 30. FIG. 8(*d*) illustrates a cut-away perspective view of the infusion pump 30 showing the electronic boards and modules that may be included in the infusion pump 30. The infusion pump 30 may include a display module 260, a mother board 262, and an interface board 264. The mother board 262 is the main control unit for the infusion pump 30, and includes the processor and memory. The display module 260 includes the display 100, and in particular embodiments, a backlight for the display 100. The interface board 264 interfaces between different systems in the infusion pump 30, and includes the drive mechanism and power supplies. The infusion pump 30 also includes a communication board 265 and an antenna 268, which enable communication with external devices, such as a remote programmer (not shown) for the infusion pump 30, the BG monitoring system 20, and the like. The communication board 265 includes the communication system as well as the relay device components. During communications with the BG monitoring system 20, the drive mechanism and power supplies on the interface board 264 are temporarily shutdown. Accordingly, the infusion pump 30 further includes a capacitor 266 for providing power to the infusion pump 30 and the communication board 265 during such communications.

Figure 10:
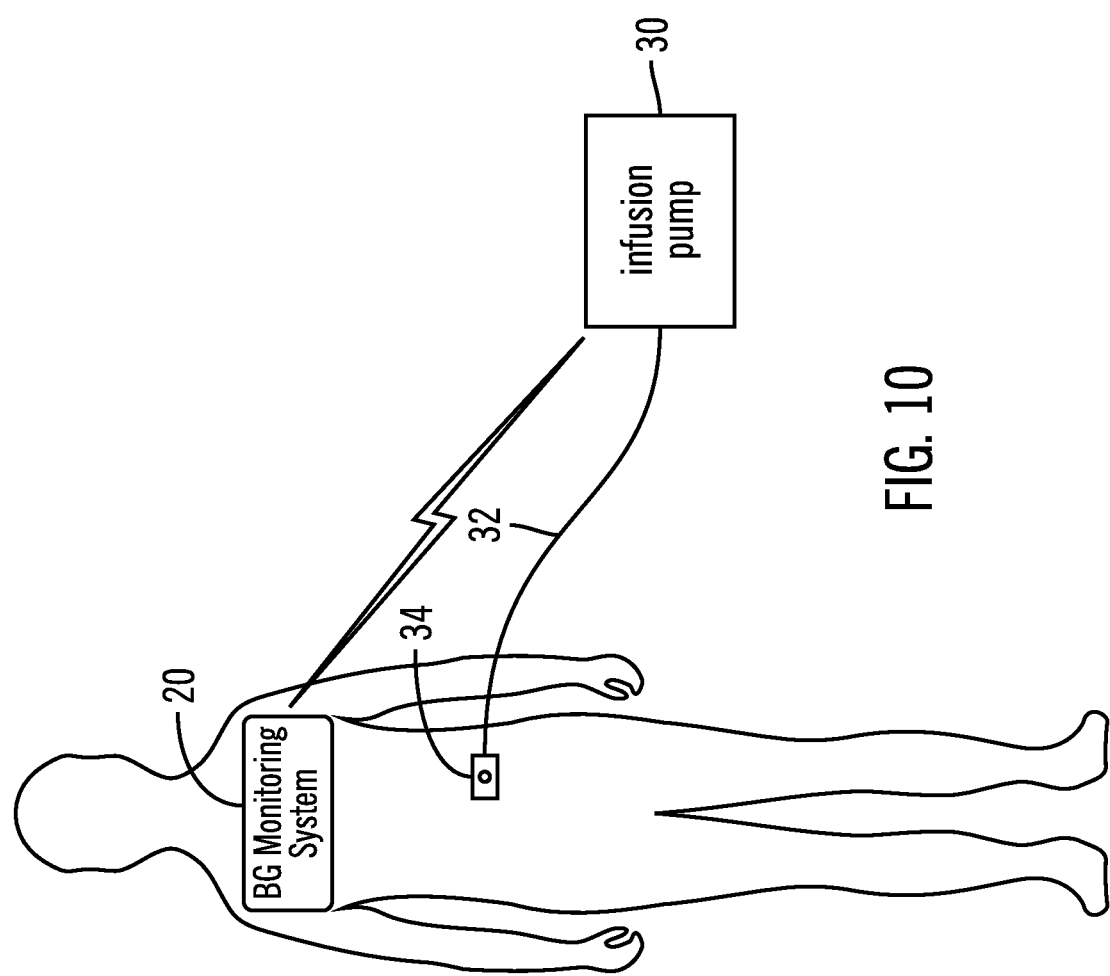
FIG. 10 is a block diagram of a system for transferring information between a blood glucose monitoring system and an infusion pump using a relay device incorporated into the infusion pump in accordance with another embodiment of the present invention.
Figure 12:
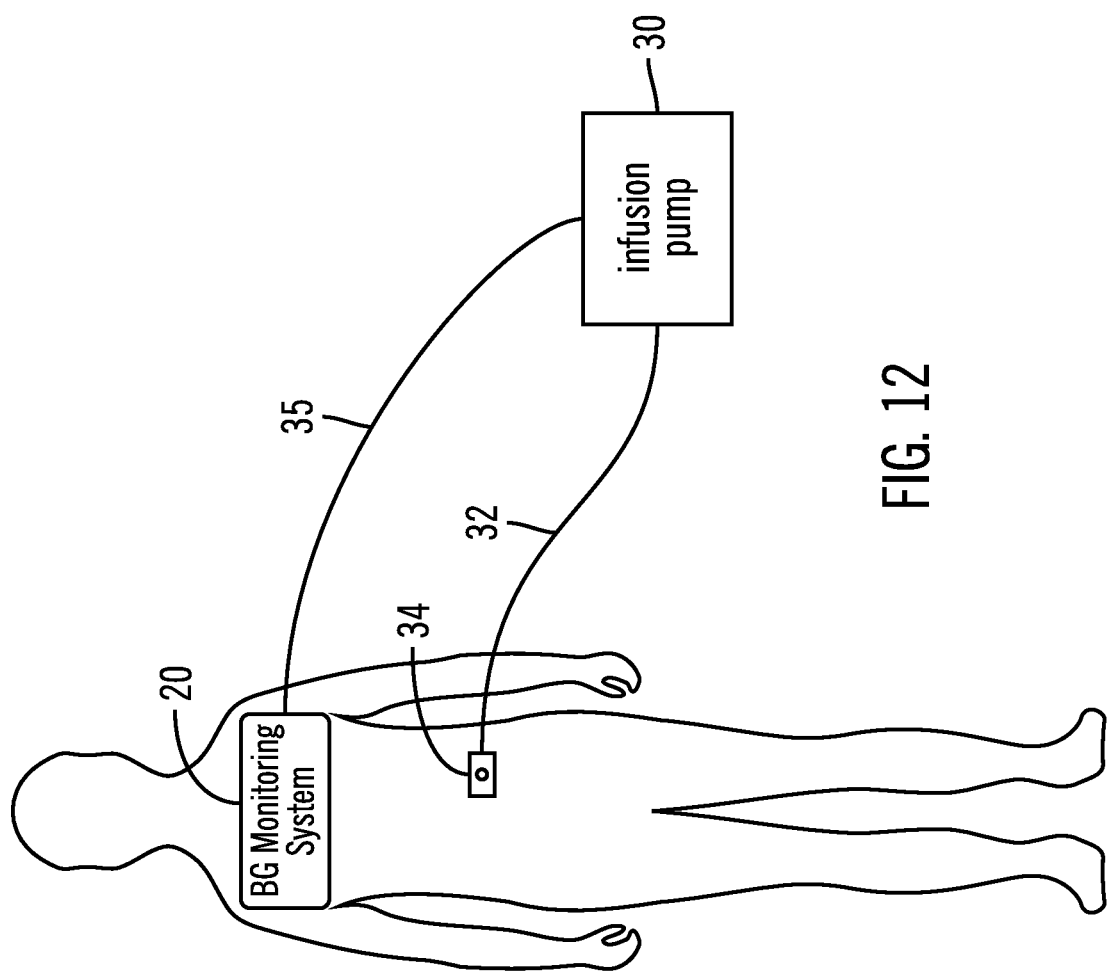
FIG. 12 is a block diagram of a system for transferring information between a blood glucose monitoring system and an infusion pump using a relay device incorporated into the infusion pump in accordance with still another embodiment of the present invention.

For example, referring to FIGS. 10-12, the relay device (not shown) may be incorporated into the infusion pump 30. The BG monitoring system 20 may transmit communications to the infusion pump 30 in a sensor system format, the relay device incorporated into the infusion pump 30 may receive such communications and convert them to a delivery system format, and the infusion pump 30 may then process such converted communications. Conversely, the infusion pump 30 may format communications in the delivery system format, the relay device incorporated into the infusion pump 30 may convert such communications to the sensor system format and transmit such converted communications, and the BG monitoring system 20 may receive such communications in the sensor system format. In particular embodiments, the BG monitoring system 20 may communicate with the infusion pump 30 using wireless modes of communication, such as radio frequency (RF), infrared (IR), ultrasonic, sonic, optical, and the like, as shown in FIGS. 10 and 11. In other particular embodiments, the BG monitoring system 20 may communicate with the infusion pump 30 using a wired connection 35, as shown in FIG. 12.

In particular embodiments, information may be downloaded directly from the relay device 10 to a storage media through an interface, such as a transmitter, a cable, a communication station, or the like. For example, information stored by the BG monitoring system 20 and/or the infusion pump 30 may be transmitted to the relay device 10, and then downloaded from the relay device 10 to the storage media. The storage media may include one or more of a personal computer (PC), a central server, an electronic memory, a personal digital assistant (PDA), a cell phone, a laptop computer, magnetic memory, silicon memory, a data storage device, and the like. In alternative embodiments, information may be downloaded directly from the BG monitoring system 20 or the infusion pump 30 to a storage media. In further alternative embodiments, information may be downloaded to the storage media from more than one of the BG monitoring system 20, relay device 10, and infusion pump 30.

In preferred embodiments, the relay device 10 communicates with the BG monitoring system 20 and the infusion pump 30 using radio frequency (RF) communication. In alternative embodiments, other modes of communication may be used, such as infrared (IR), wired, ultrasonic, sonic, optical, and the like. In further alternative embodiments, more than one mode of communication may be utilized by the relay device 10.

In preferred embodiments, the relay device 10 includes an RF mixer 300, a first microcontroller 302, a second microcontroller 304, and an RF transceiver 306, as shown in FIG. 9(*a*). The RF mixer 300 receives an RF signal from the BG monitoring system 20 and forwards the signal to the first microcontroller 302. The first microcontroller 302 decodes the RF signal received in a first format from the BG monitoring system 20 (e.g., at a frequency of 131 kilohertz), and forwards the decoded signal to the second microcontroller 304. Next, the second microcontroller 304 processes and encodes the signal into a second format for the infusion pump 30 (e.g., at a frequency of 916 megahertz), and forwards the encoded signal to the RF transceiver 306. The RF transceiver 306 then transmits the encoded signal to the infusion pump 30. Conversely, the RF transceiver 306 receives an RF signal from the infusion pump 30 and forwards the signal to the second microcontroller 304. The second microcontroller 304 decodes the RF signal received in the second format from the infusion pump 30, and forwards the decoded signal to the first microcontroller 302. Next, the first microcontroller 302 processes and encodes the signal into the first format for the BG monitoring system 20, and forwards the encoded signal to the RF mixer 300. The RF mixer 300 then transmits the encoded signal to the BG monitoring system 20. Inclusion of the two microcontrollers 302 and 304 allows the relay device 10 to encode and decode signals for the BG monitoring system 20 and the infusion pump 30 simultaneously.

In alternative embodiments, the two microcontrollers 302 and 304 shown in FIG. 9(*a*) may be replaced with a single fast microcontroller 308, as illustrated in FIG. 9(*b*). The fast microcontroller 308 encodes and decodes signals in appropriate formats respectively for the BG monitoring system 20 and the infusion pump 30 in a manner similar to that of the two microcontrollers 302 and 304 shown in FIG. 9(*a*). In further alternative embodiments, the relay device 10" may include an RF mixer 320 and an RF transceiver 326, as illustrated in FIG. 9(*c*), which are similar to the RF mixer 300 and RF transceiver 306 shown in FIGS. 9(*a*) and 9(*b*). The relay device 10" may also include a field programmable gate array (FPGA) 322, which performs functions similar to the first microcontroller 302 shown in FIG. 9(*a*), for encoding and decoding signals in an appropriate format for the BG monitoring system 20. The relay device 10" may further include a microcontroller 322, which is similar to the second microcontroller 304 shown in FIG. 9(*a*), for encoding and decoding signals in an appropriate format for the infusion pump 30.

Figure 9D:
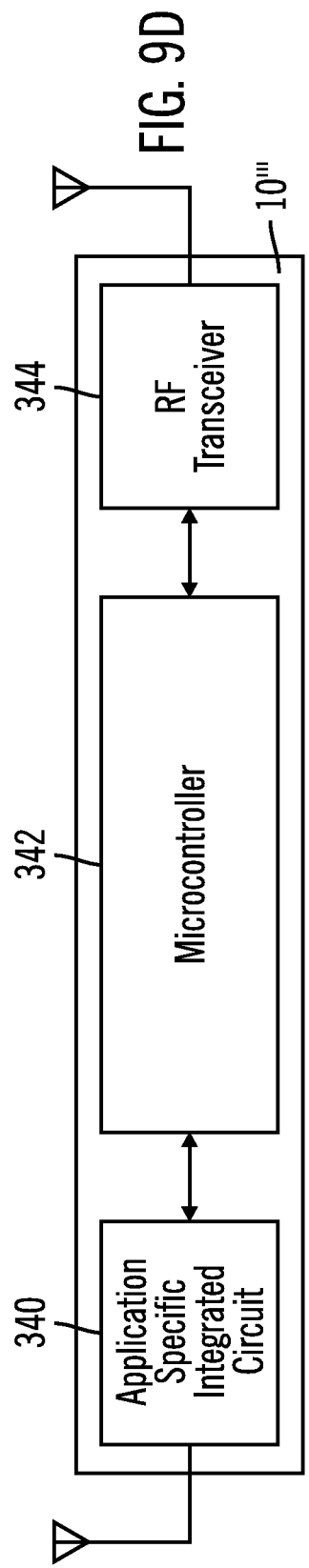
Figure 9E:
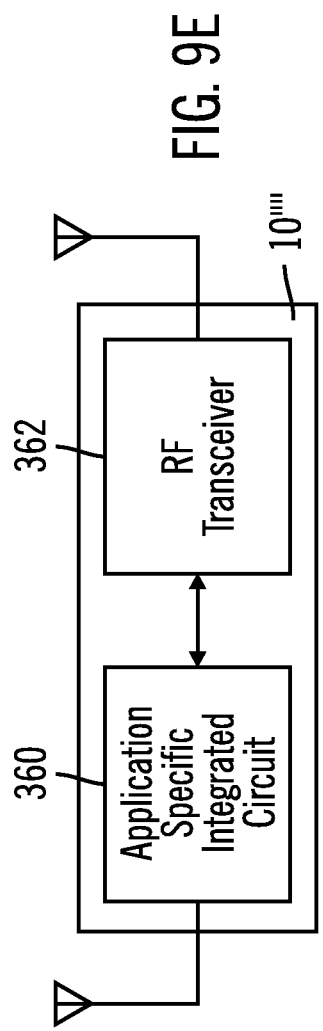

In other alternative embodiments, the relay device 10'" may include an application specific integrated circuit (ASIC) 340, which incorporates an RF mixer for transmitting and receiving signals to and from the BG monitoring system 20, as illustrated in FIG. 9(*d*). The ASIC 340 may also encode and decode information in an appropriate format for the BG monitoring system 20. Additionally, the relay device 10'" may include a microcontroller 342, which is similar to the second microcontroller 304 shown in FIG. 9(*a*), for encoding and decoding signals in an appropriate format for the infusion pump 30. The relay device 10'" may further include an RF transceiver 344, which is similar to the RF transceiver 306 shown in FIG. 9(*a*), for transmitting and receiving signals to and from the infusion pump 30. In still other alternative embodiments, the microcontroller 342 shown in FIG. 9(d) may be omitted, and the functionality instead may be included in an application specific integrated circuit (ASIC_360, as shown in FIG. 9(e). The ASIC 360 transmits and receives signals to and from the BG monitoring system 20. The ASIC 360 also encodes and decodes signals in appropriate formats respectively for the BG monitoring system 20 and infusion pump 30. The relay device 10"" may further include an RF transceiver 362, which is similar to the RF transceiver 306 shown in FIG. 9(a), for transmitting and receiving signals to and from the infusion pump 30.

Referring to FIG. 1, the relay device 10 receives information from the BG monitoring system 20 in a sensor system format, converts the information into a delivery system format appropriate for the infusion pump 30, and then transmits the converted information in the delivery system format to the infusion pump 30. The relay device 10 may also receive information from the infusion pump 30 in the delivery system format, convert the information into the sensor system format appropriate for the BG monitoring system 20, and then transmit the converted information in the sensor system format to the BG monitoring system 20. In alternative embodiments, communication is in only one direction, either from the BG monitoring system 20 to the infusion pump 30, or from the infusion pump 30 to the BG monitoring system 20.

In preferred embodiments, the sensor system and delivery system formats include one or more frequencies, communication protocols, and the like that are used to transfer information between the BG monitoring system 20 and the infusion pump 30. For example, the sensor system format utilized by the BG monitoring system 20 may include a lower frequency, such as 131 kilohertz, resulting in less tissue attenuation at and/or near the insertion site of the BG monitoring sensor set 50. The delivery system format utilized by the infusion pump 30 may include a higher frequency, such as 916 megahertz or 402-405 megahertz, ensuring compliance with federal, state, regulatory, and other requirements for RF communications. However, other frequencies may be utilized by the BG monitoring system 20 and/or infusion pump 30.

The communication protocols specify carrier media for communication, such as radio frequency (RF) (including frequency modulated (FM), amplitude modulated (AM), and the like RF), infrared (IR), ultrasonic, audio, light wave, Bluetooth, IRDA, conductive using wires or other direct contacts, and the like. The communication protocols also specify information packaging, which includes how the information is arranged and sent on the carrier media. For example, the information packaging may specify which data components are sent (e.g., the serial number of the relay device 10, BG monitoring system 20, and/or infusion pump 30, a date and time stamp, a sensor measurement, a pump command, and the like). The information packaging may also specify the order in which data components are sent. Further, the information packaging may specify how the information is sent, such as in packets, bits, words, and the like. The information packaging may additionally specify how the information is expressed, such as in decimal, hexadecimal, DC balanced format, and the like.

The BG monitoring system 20 utilizes a sensor system communication protocol, and the infusion pump 30 utilizes a delivery system communication protocol. For example, the BG monitoring system 20 uses the sensor system communication protocol to communicate with the relay device 10, and the infusion pump 30 uses the delivery system communication protocol to communicate with the relay device 10. In particular embodiments, the BG monitoring system 20 and infusion pump 30 do not use the same communication protocol; thus, the relay device 10 converts information received from the BG monitoring system 20 into the delivery system communication protocol for communicating to the infusion pump 30, and the relay device 10 converts information received from the infusion pump 30 into the sensor system communication protocol for communicating to the BG monitoring system 20. For example, the relay device 10 may receive BG data or measurements from the BG monitoring system 20 formatted in the sensor system communication protocol utilizing radio frequency carrier media, in packets of 107 bytes, or the like. The relay device 10 converts such data or measurements into the delivery system communication protocol utilizing infrared carrier media, in packets of 71 bytes, or the like, and then transmits such converted data or measurements formatted in the delivery system communication protocol to the infusion pump 30. However, other carrier media or information packaging may be utilized by the BG monitoring system 20 and/or infusion pump 30.7

In preferred embodiments, the relay device 10, BG monitoring system 20, infusion pump 30, and other devices capable of communicating with the relay device 10, BG monitoring system 20, and/or infusion pump 30 (e.g., remote programmer for the BG monitoring system 20, remote programmer for the infusion pump 30, and the like) each have a unique identification (ID) code, such as a serial number, identification number, password, or the like. The ID code may be included in communications transmitted to and received from the relay device 10, BG monitoring system 20, and/or infusion pump 30 in order to ensure security and/or to distinguish information from various sources. In particular embodiments, each packet of information that is transmitted to the relay device 10 may include the ID code for the relay device 10, and the relay device 10 may use the ID code to discern whether the packet of information is intended for the relay device 10. Similarly, each packet of information that is transmitted to the BG monitoring system 20 may include the ID code for the BG monitoring system 20, and the BG monitoring system 20 may use the ID code to discern whether the packet of information is intended for the BG monitoring system 20. Also, each packet of information that is transmitted to the infusion pump 30 may include the ID code for the infusion pump 30, and the infusion pump 30 may use the ID code to discern whether the packet of information is intended for the infusion pump 30. In further particular embodiments, the relay device 10, BG monitoring system 20, infusion pump 30, and other devices capable of communicating with the relay device 10, BG monitoring system 20, and/or infusion pump 30 may know each other's unique ID code. The BG monitoring system 20 and/or the infusion pump 30 may respond to commands and accept information only from devices for which they know such ID codes. For example, the BG monitoring system 20 may communicate with the infusion pump 30 through the relay device 10, and thus, may know the ID codes for the relay device 10 and infusion pump 30. Conversely, the infusion pump 30 may communicate with the BG monitoring system 20 through the relay device 10, and thus, may know the ID codes for the relay device 10 and BG monitoring system 20. The infusion pump 30 may also know the ID code for a remote programmer. In alternative embodiments, the relay device 10, BG monitoring system 20, infusion pump 30, and other devices capable of communicating with the BG monitoring system 20 and/or infusion pump 30 have no ID code.

In preferred embodiments, the BG monitoring system 20 is continually synchronized with any device that communicates with the BG monitoring system 20, such as the relay device 10, the infusion pump 30 via the relay device 10, and the like. The BG monitoring system 20 transmits information at fixed intervals (e.g., once every thirty seconds, minute, five minutes, ten minutes, twenty minutes, or the like) for exact time periods (e.g., for time periods of less than one second, one second, one to five seconds, more than five seconds, or the like). The devices that communicate with the BG monitoring system 20 "wake up" at the fixed intervals and "listen" to receive the information from the BG monitoring system 20. This fixed interval communication method allows the BG monitoring system 20 and the devices that communicate with the BG monitoring system 20 to supply power to their communication systems on a periodic, rather than continuous, basis. Accordingly, the BG monitoring system 20 and the devices that communicate with the BG monitoring system 20 are able to save power when not communicating with one another. In alternative embodiments, the BG monitoring system 20 and the devices that communicate with the BG monitoring system 20 may supply power to their communication systems on a continuous basis, and thus, be capable of continuous communication. In further alternative embodiments, the BG monitoring system 20 and the devices that communicate with the BG monitoring system 20 may supply power to their communication systems only upon request from the user. For example, the user may select the dedicated key 122 on the infusion pump 30 shown in FIG. 3(a), or alternatively, the dedicated key 212 or 226 on the relay device 10 shown in FIGS. 6(c) and 6(d), to request information from the BG monitoring system 20. The BG monitoring system 20 may periodically supply power to its communication system for a relatively short time period in order to detect whether another device is requesting information, and in response to such a request, the BG monitoring system 20 and the devices that communicate with the BG monitoring system 20 may supply power to their communication systems and then communicate the requested information. Accordingly, the BG monitoring system 20 and the devices that communicate with the BG monitoring system 20 are able to save power when not communicating with one another.

Figure 3A:
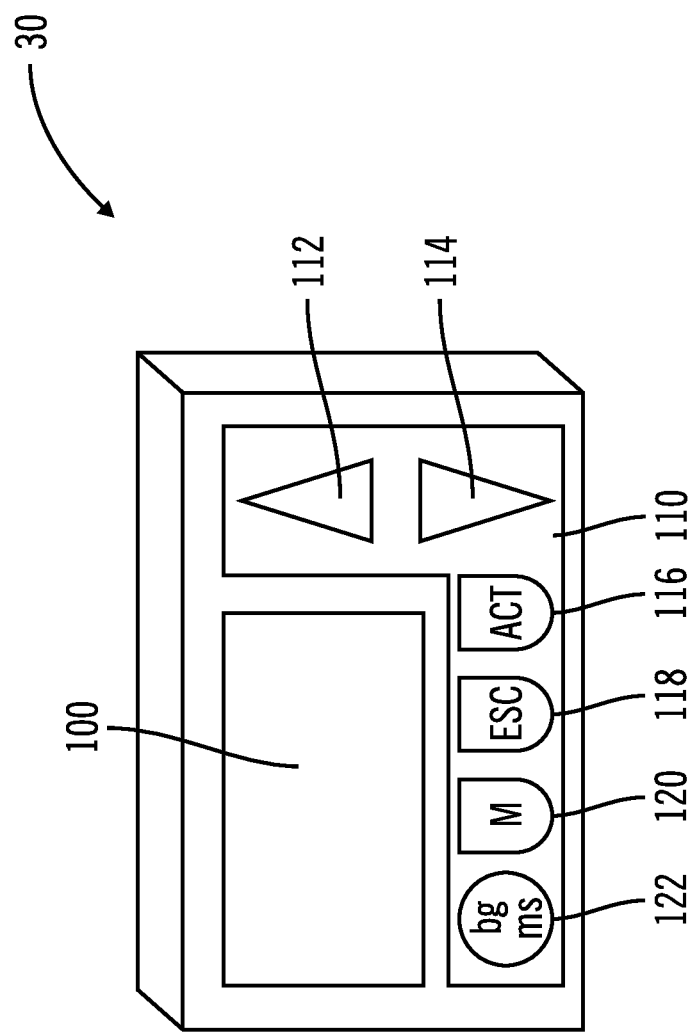
FIG. 3(a) is a perspective view of an external infusion pump in accordance with an embodiment of the present invention.
Figure 3B:
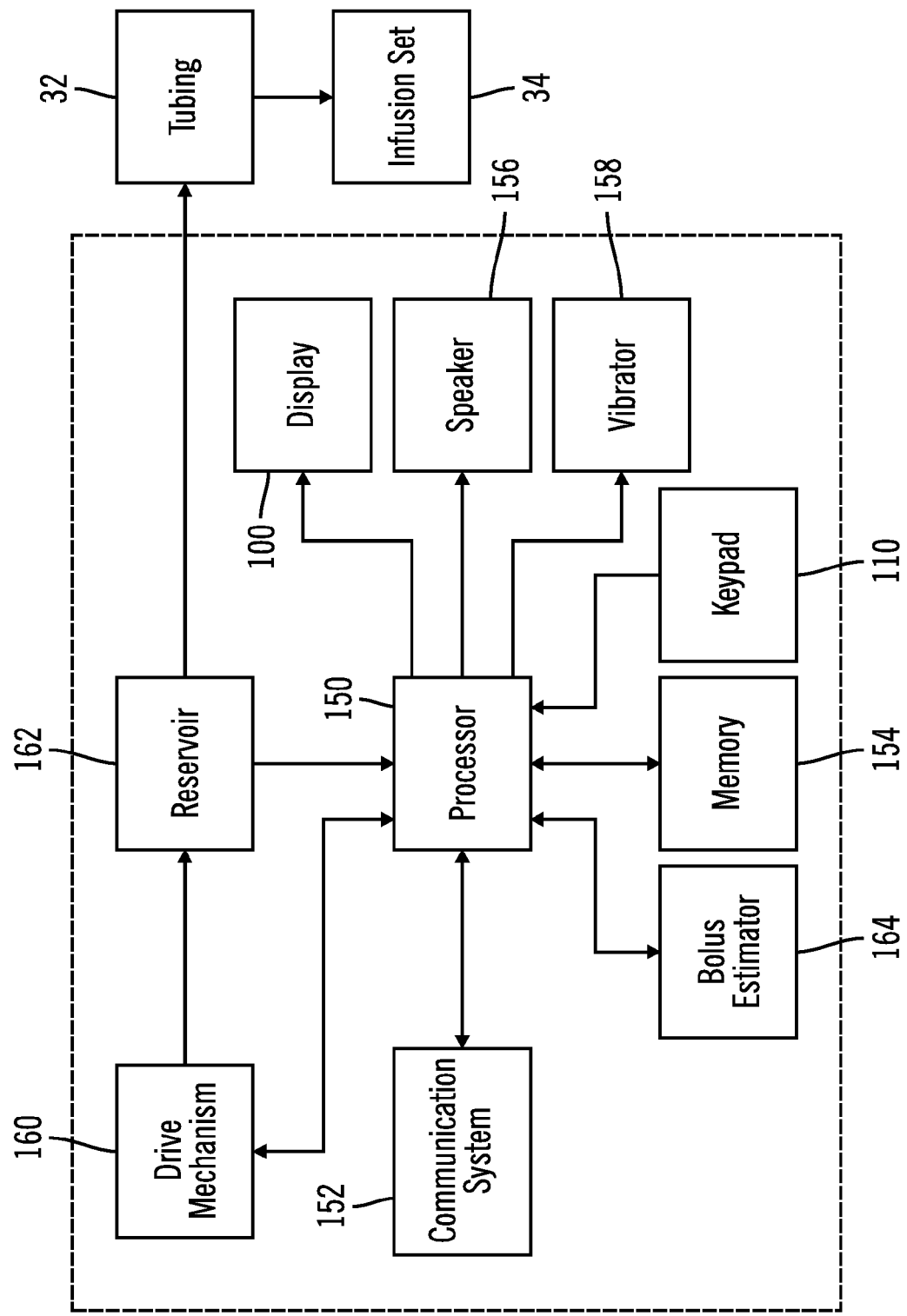
FIG. 3(b) is a simplified block diagram of an external infusion pump in accordance with an embodiment of the present invention.
Figure 4A:
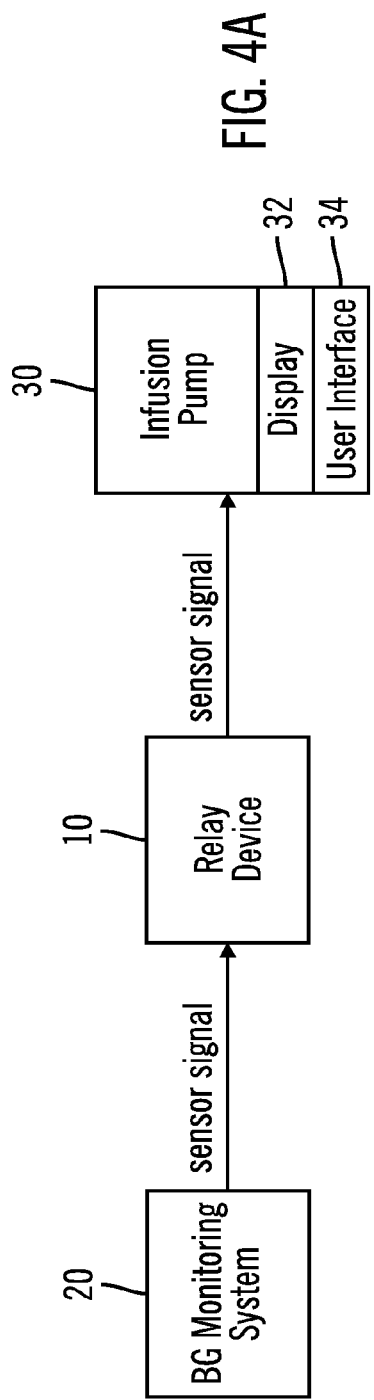
FIGS. 4(a)-5(f) are block diagrams of a system for transferring information between a blood glucose monitoring system and an infusion pump through a relay device in accordance with embodiments of the present invention.

Referring to FIG. 1, the relay device 10 receives information from the BG monitoring system 20, and then transmits the information to the infusion pump 30. The relay device 10 may also receive information from the infusion pump 30, and then transmit the information to the BG monitoring system 20. In preferred embodiments, the infusion pump 30 includes a display 32 and a user interface 34, as shown in FIG. 4(a). For example, the display 32 may be an LCD display 100, and the user interface 34 may be a keypad 110 including one or more keys, as shown in FIGS. 3(a)-3(b). The BG monitoring system 20 sends a sensor signal to the relay device 10, and then the relay device 10 sends the sensor signal to the infusion pump 30. In preferred embodiments, the sensor signal contains uncalibrated sensor data, and the infusion pump 30 calibrates the uncalibrated sensor data to generate sensor measurements, which are shown on the display 32. In particular embodiments, the BG monitoring system automatically sends the sensor data to the infusion pump 30 on a periodic (e.g., once every thirty seconds, minute, five minutes, ten minutes, or the like) or continuous basis, and the infusion pump 30 automatically shows the sensor measurement on the display 32 once the sensor data has been received and calibrated. The user may also utilize the user interface 34 to cause the display 32 to show a sensor measurement. In other particular embodiments, once the infusion pump 30 generates the sensor measurement, the infusion pump 30 may provide an alarm or warning to the user if the sensor measurement is above or below target glycemic values. For example, if the sensor measurement is above a hyperglycemic limit (e.g., 250 mg/dl) or below a hypoglycemic limit (e.g., 70 mg/dl), the infusion pump 30 may provide the user with a visible alarm via the display 100 and/or lights, an audible alarm via the speaker 156, and/or a vibration alarm via the vibrator 158. The infusion pump 30 may also suspend insulin delivery if the sensor measurement is below the hypoglycemic limit, and notify the user to activate a bolus delivery if the sensor measurement is above the hyperglycemic limit. In further particular embodiments, the infusion pump 30 may include the bolus estimator 164, which utilizes the sensor measurement to estimate an appropriate amount of insulin to be delivered to the user based on the user's BG level, the amount of carbohydrates to be consumed, and the like. The calculated bolus estimate may be shown to the user on the display 32, and the user may then utilize the user interface 34 to accept or modify the bolus estimate for infusion into the user. In alternative embodiments, the BG monitoring system 20 calibrates the sensor data to generate sensor measurements, which are included in the sensor signal transmitted from the BG monitoring system 20 to the infusion pump 30 via the relay device 10. In other alternative embodiments, the BG monitoring system 20 sends a sensor signal with uncalibrated sensor data to the relay device 10, the relay device 10 calibrates the uncalibrated sensor data to generate sensor measurements, and the relay device 10 sends the sensor signal with the sensor measurements to the infusion pump 30.

Figure 4B:
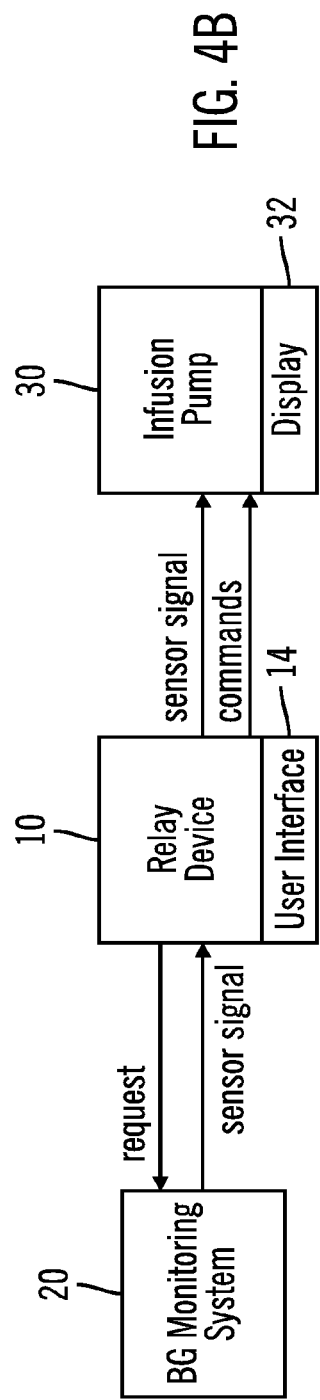
Figure 4C:
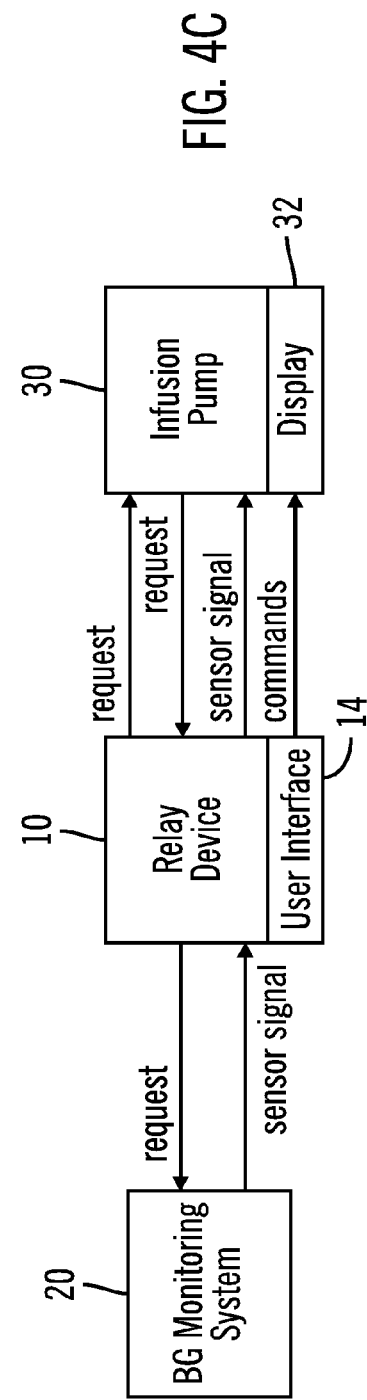
Figure 6A:
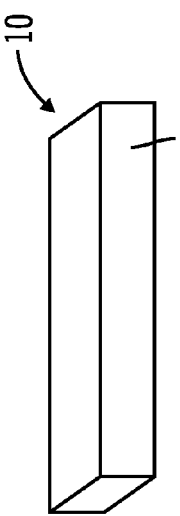
FIGS. 6(a)-6(d) are perspective views of a relay device in accordance with embodiments of the present invention.
Figure 6B:
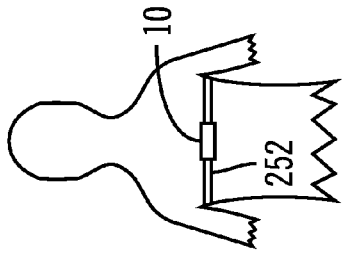
Figure 6C:
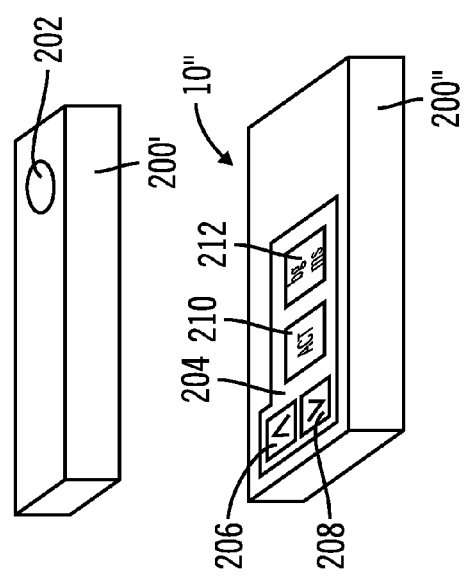
Figure 6D:
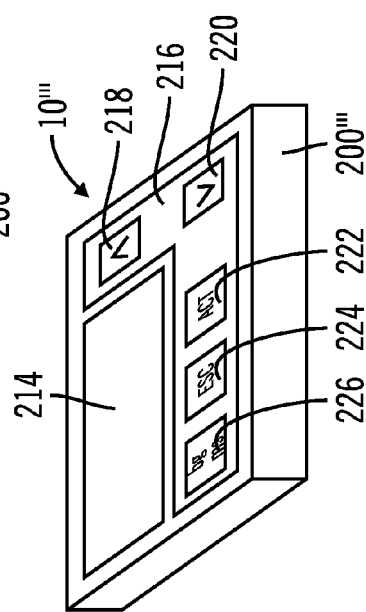
Figure 8D:
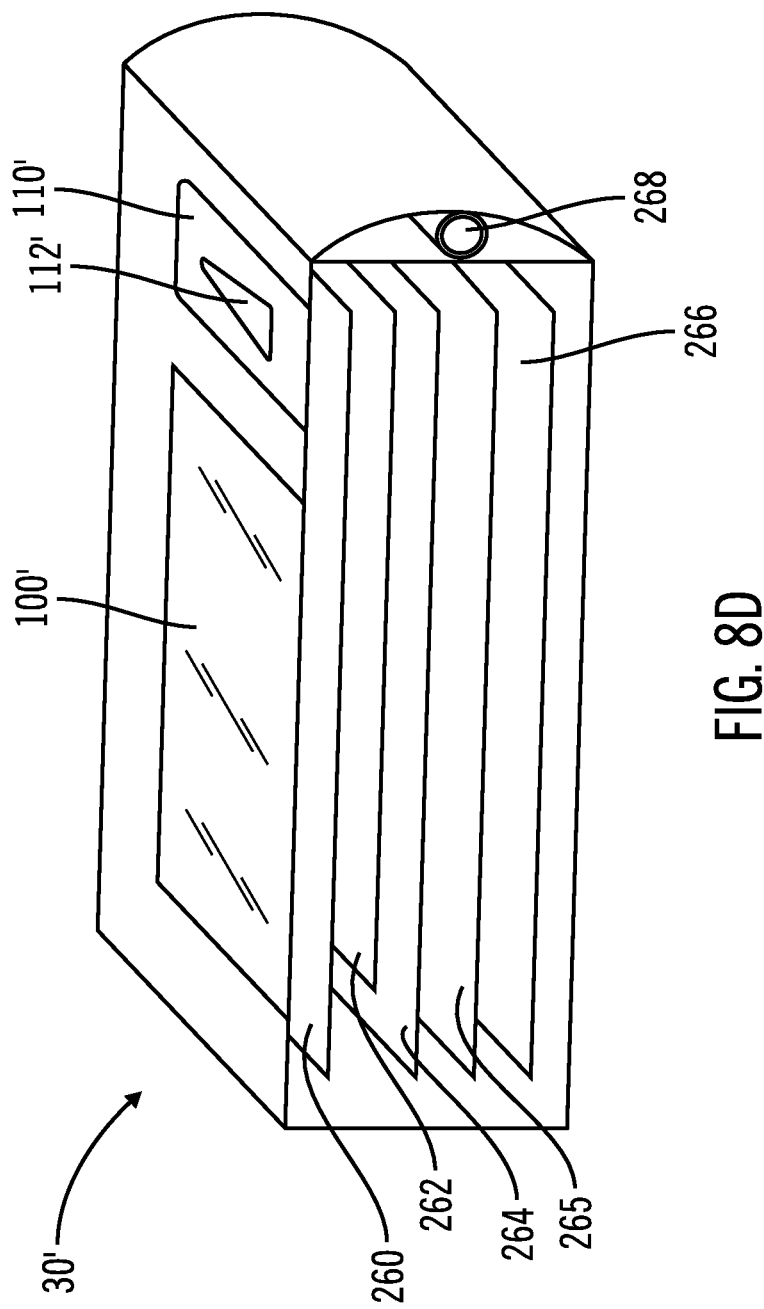
FIG. 8(d) is a cut-away perspective view of an infusion pump with a relay device included in the infusion pump in accordance with another embodiment of the present invention.

In additional alternative embodiments, the infusion pump 30 may include a display 32, and the relay device 10 may include a user interface 14, as shown in FIG. 4(b). For example, the display 32 may be an LCD display 100 (as shown in FIGS. 3(a)-3(b)), and the user interface 14 may be a single key 202 (as shown in FIG. 6(b)), or a keypad 204 or 216 including one or more keys (as shown in FIGS. 6(c) and 6(d)). The user may utilize the user interface 14 on the relay device 10 to request new data from the BG monitoring system 20. When the user interface 14 is activated (e.g., the user presses the single key 202 shown in FIG. 6(b), one or more keys on the keypad 204 shown in FIG. 6(c), or one or more keys on the keypad 216 shown in FIG. 6(d)), the relay device 10 sends a request to the BG monitoring system 20 to transmit the most recent sensor data, as shown in FIG. 4(b). In other alternative embodiments, when the user interface 14 is activated, the relay device 10 sends a signal to the infusion pump 30 to request the most recent sensor data from the BG monitoring system 20, and the infusion pump 30 then sends such a request to the BG monitoring system 20 through the relay device 10, as shown in FIG. 4(c). Referring to FIGS. 4(b) and 4(c), in response to a request for the most recent sensor data, the BG monitoring system 20 sends a sensor signal to the relay device 10, and then the relay device 10 sends the sensor signal to the infusion pump 30, similar to the manner described above with respect to FIG. 4(a). In particular embodiments, the infusion pump 30 may automatically show a sensor measurement on the display 32 once the sensor signal is received by the infusion pump 30. The user may also utilize the user interface 14 on the relay device 10 to cause the display 32 on the infusion pump 30 to show a sensor measurement. The user may also utilize the user interface 14 on the relay device 10 to send commands or data to the infusion pump 30.

In further alternative embodiments, the relay device 10 may include a first user interface 14', and the infusion pump 30 may include a display 32 and a second user interface 34', as shown in FIG. 4(f). The user may utilize the first user interface 14' on the relay device 10 to request new data from the BG monitoring system 20. When the first user interface 14' is activated, the relay device 10 sends a request to the BG monitoring system 20 to transmit the most recent sensor data. In response, the BG monitoring system 20 sends a sensor signal to the relay device 10, and then the relay device 10 sends the sensor signal to the infusion pump 30, similar to the manner described above with respect to FIG. 4(a). In particular embodiments, the infusion pump 30 may automatically show a sensor measurement on the display 32' once the sensor signal is received by the infusion pump 30. The user may also utilize the first user interface 14' on the relay device 10 or the second user interface 34' on the infusion pump 30 to cause the display 32 on the infusion pump 30 to show a sensor measurement. The user may additionally utilize the first user interface 14' on the relay device 10 to send commands or data to the infusion pump 30. Further, the user may utilize the second user interface 34' on the infusion pump 30 to perform functions on the infusion pump 30.

In other alternative embodiments, the relay device 10 may include a display 12 and a user interface 14, as shown in FIG. 4(d). For example, the display 12 may be an LCD display 214, and the user interface 14 may be a keypad 216 including one or more keys, as illustrated in FIG. 6(d). The BG monitoring system 20 sends a sensor signal with uncalibrated sensor data to the relay device 10, and the relay device 10 calibrates the data to generate sensor measurements, which are shown on the display 12 of the relay device 10. In particular embodiments, the relay device 10 may automatically show a sensor measurement on the display 12 once the sensor data is received and calibrated by the relay device 10. The user may also utilize the user interface 14 to cause the display 12 to show a sensor measurement. The user may further utilize the user interface 14 on the relay device 10 to send commands or data to the infusion pump 30. In particular embodiments, the relay device 10 may also receive data from the infusion pump 30 (not shown), such as the amount of insulin remaining, alarms indicating a low battery or no delivery by the infusion pump 30, and the like. The relay device 10 may then utilize such data to adjust the commands sent to the infusion pump 30 and/or show such data on the display 12 to the user. In alternative embodiments, the BG monitoring system 20 calibrates the sensor data to generate sensor measurements, which are included in the sensor signal transmitted from the BG monitoring system 20 to the relay device 10.

Figure 2B:
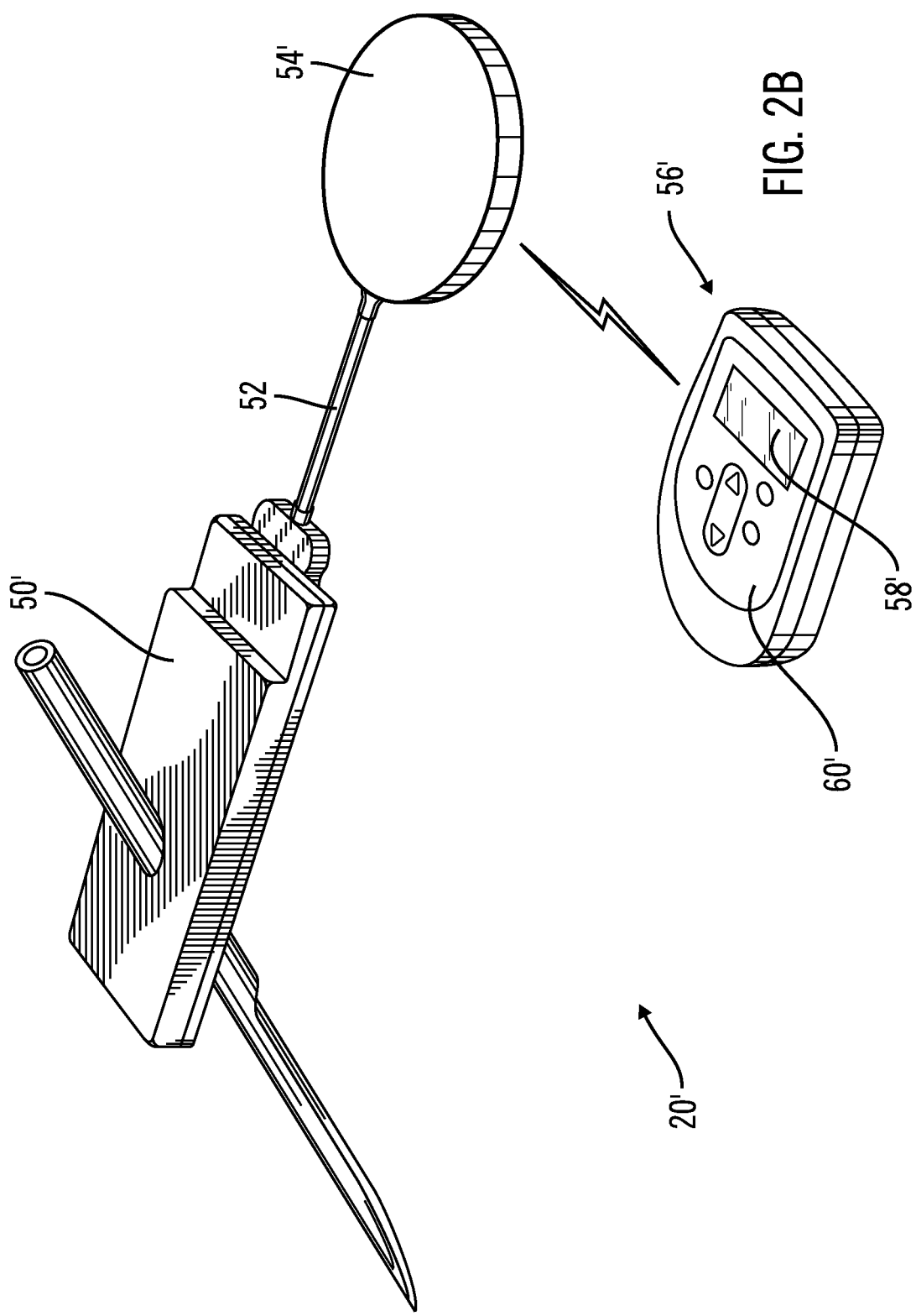
Figure 2C:
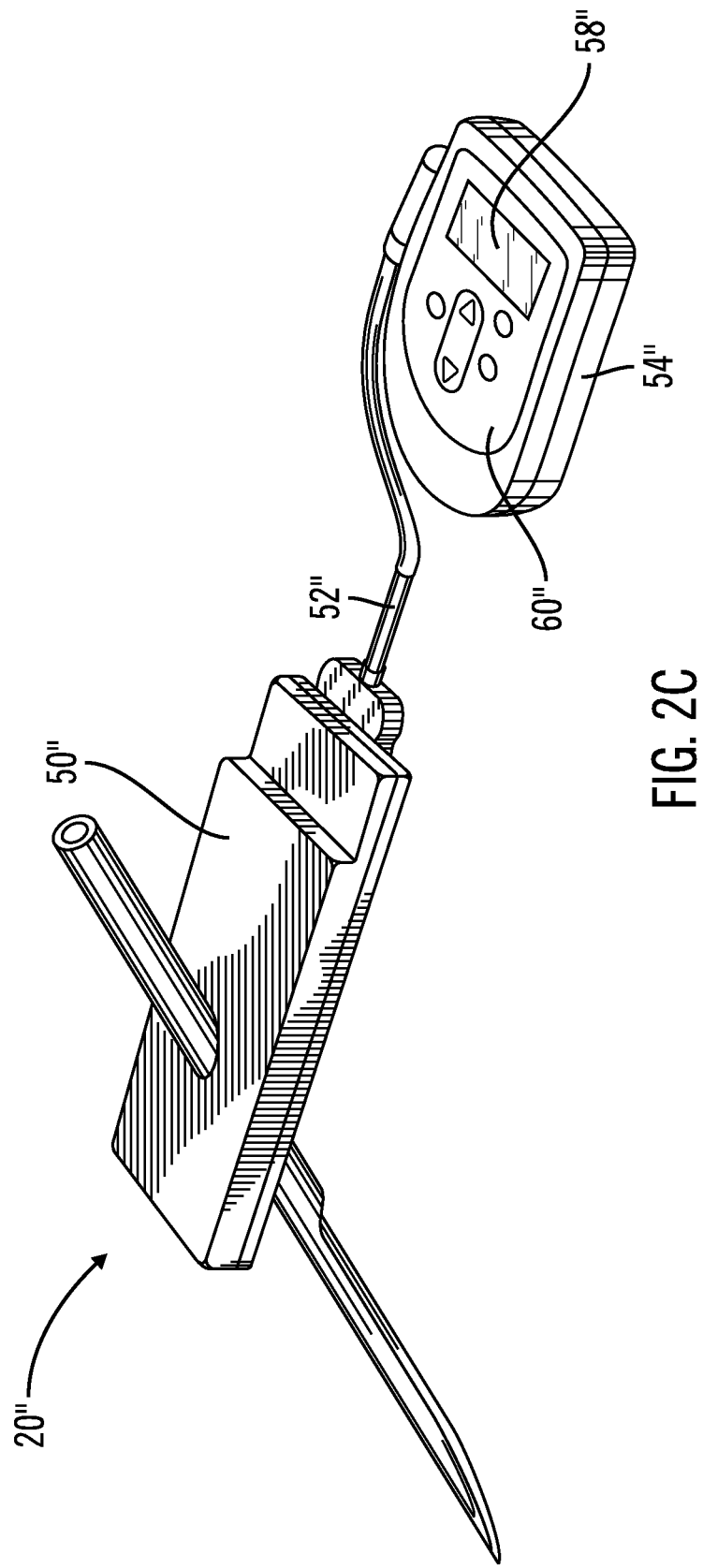

In still other alternative embodiments, the BG monitoring system 20 includes a display 22 and a user interface 24, as shown in FIG. 4(e). For example, the display 22 may be an LCD display 58, and the user interface 24 may be a keypad 60 including one or more keys, as shown in FIGS. 2(a)-2(c). The BG monitoring system 20 calibrates the sensor data to generate sensor measurements, which are shown on the display 22 of the BG monitoring system 20. In particular embodiments, the BG monitoring system 20 may automatically show a sensor measurement on the display 22 once the sensor data is calibrated. The user may also utilize the user interface 24 to cause the display 22 to show a sensor measurement. The user may further utilize the user interface 24 on the BG monitoring system 20 to send commands or data through the relay device 10 to the infusion pump 30.

In preferred embodiments, the BG monitoring system 20 sends a sensor signal to the relay device 10, and then the relay device 10 sends the sensor signal to the infusion pump 30, as shown in FIG. 4(a). The infusion pump 30 includes a display 32 and a user interface 34, such as the display 100 and user interface 110 shown in FIG. 3(a). In particular embodiments, the BG monitoring system automatically sends the sensor signal to the infusion pump 30 on a periodic (e.g., once every thirty seconds, minute, five minutes, ten minutes, or the like) or continuous basis. In other particular embodiments, the infusion pump 30 periodically sends a command signal to the BG monitoring system 20 via the relay device 10, commanding the BG monitoring system 20 to send the sensor signal to the infusion pump 30, and in response to the command, the BG monitoring system 20 sends the sensor signal to the infusion pump 30. In further particular embodiments, the user interface 110 may be utilized to cause the BG monitoring system 20 to send the sensor signal to the infusion pump 30 via the relay device 10. In preferred embodiments, the infusion pump 30 automatically shows a sensor measurement on the display 32 once the sensor signal is received by the infusion pump 30. The user may also utilize the user interface 110 to cause the display 100 to show a sensor measurement.

The user interface 110 on the infusion pump 30 preferably includes a dedicated interface for requesting information from and/or inputting data to the BG monitoring system 20 via the relay device 10. Additionally, in particular embodiments where bi-directional communication is not enabled continuously between the BG monitoring system 20 and the infusion pump 30, utilizing the dedicated interface may initiate bi-directional communication between the infusion pump 30 and the BG monitoring system 20 via the relay device 10. In further particular embodiments, the dedicated interface may be used to cause the display 100 of the infusion pump 30 to show historical data, such as trends of whether sensor measurements are increasing or decreasing, a plot of two or more sensor measurements, a graph of the past n-hours of sensor measurements, and the like. In other embodiments, the infusion pump 30 may automatically show sensor measurements or historical data (e.g., trends, plots, graphs, or the like of sensor measurements) on the display 100 when the display 100 would otherwise be blank.

Referring to FIG. 3(a), the dedicated interface on the infusion pump 30 may include a dedicated key 122 for causing the display 100 to show the sensor measurement. In alternative embodiments, the user may select one or more keystrokes to cause the display 100 to show the sensor measurement. For example, the user may select the dedicated key 122 followed by the ACT key 116 to cause the display 100 to show the sensor measurement. In further alternative embodiments, the ability of the infusion pump 30 to communicate with the BG monitoring system 20 via the relay device 10 may be activated by entering the BG monitoring system's 20 serial number or other identifying information into the infusion pump 30. In response, the infusion pump 30 may program certain keys for interfacing with the BG monitoring system 20 via the relay device 10.

In other alternative embodiments, the dedicated interface may include a button, switch, lever, handle, touch screen, or the like, or combinations of keys, buttons, switches, levers, handles, touch screens, or the like. Combinations of interfaces include activating more than one interface simultaneously (in parallel), or activating more than one interface in sequence. In still other alternative embodiments, the dedicated interface may be located on another device that communicates with the infusion pump 30, and the sensor measurement may be shown on a display of that device, such as the BG monitoring system 20 (for example, the glucose monitor 54 and/or data processor 56), a remote programmer (not shown) for the infusion pump 30, a personal digital assistant (PDA), a computer, a cell phone, or the like.

In preferred embodiments, one or more sensor measurements are stored in the memory 154 of the infusion pump 30. Furthermore, selecting the dedicated key 122 (or other dedicated interface) causes the most recent sensor measurement to be shown on the display 100. When the most recent sensor measurement is already shown on the display 100, selecting the dedicated key 122 causes the next, most recent sensor measurement to be shown on the display 100, and each subsequent selection of the dedicated key 122 causes older and older sensor measurements to be shown on the display 100. In alternative embodiments, the infusion pump 30 may include other user interfaces to display older sensor measurements. In other alternative embodiments, the sensor measurements may be stored in a storage device other than the infusion pump 30, and selecting the dedicated key 122 causes the infusion pump 30 to retrieve the sensor measurement from the storage device and then show it on the display 100.

In additional alternative embodiments, the infusion pump 30 periodically sends a command signal to the BG monitoring system 20 via the relay device 10, commanding the BG monitoring system 20 to send sensor data to the infusion pump 30, so that the most recent sensor data is available to be shown on the display 100 of the infusion pump 30. In response to the command from the infusion pump 30, the BG monitoring system 20 sends the sensor data to the infusion pump 30, and the infusion pump 30 calibrates the sensor data to generate a sensor measurement. The sensor measurement is then stored in the memory 154 of the infusion pump 30. When the user desires to see the most recent sensor measurement, the user selects the dedicated key 122 (or other dedicated interface) to retrieve the sensor measurement from the memory 154 of the infusion pump 30 and show the sensor measurement on the display 100 of the infusion pump 30. In other alternative embodiments, the sensor data is stored in the memory 154 of the infusion pump 30. When the user selects the dedicated key 122 to view the sensor measurement, the sensor data is retrieved from the memory 154 of the infusion pump 30, and then calibrated to generate the sensor measurement. In further alternative embodiments, the BG monitoring system 20 sends calibrated sensor measurements to be stored in the memory 154 of the infusion pump 30. In yet other alternative embodiments, the infusion pump 30 communicates with the BG monitoring system 20 to indicate that the sensor data has been received and/or to echo the sensor data so that the data can be retransmitted if it was received inaccurately.

In still other alternative embodiments, the dedicated key 122 (or other dedicated interface) is used to cause the BG monitoring system 20 to send the most recent sensor data, such as one or more raw sensor data points, one or more calibrated sensor measurements, or the like, to the infusion pump 30. Once the sensor data is received, the infusion pump 30 shows the most recent sensor measurement on the display 100. In particular alternative embodiments, the infusion pump 30 indicates to the BG monitoring system 20 the most recent sensor data that the infusion pump 30 has received, and in response, the BG monitoring system 20 sends any additional sensor data that the BG monitoring system 20 has that has not been received by the infusion pump 30.

Figure 5A:
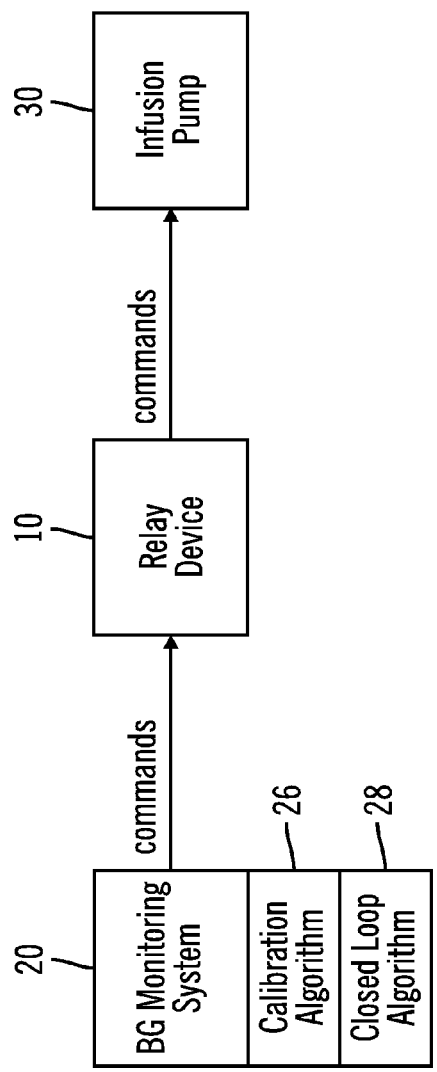
Figure 5B:
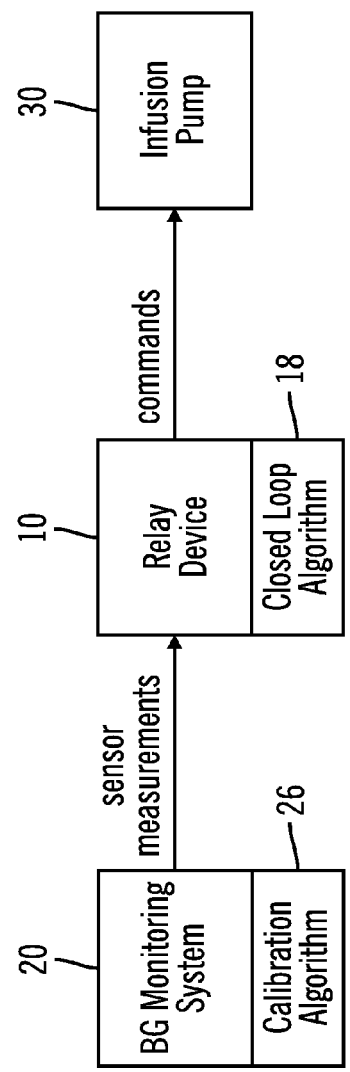
Figure 5C:
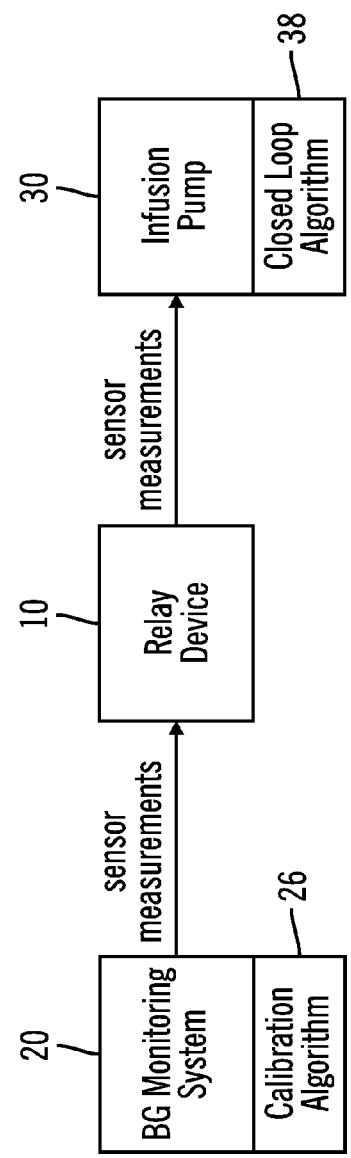

In another embodiment of the present invention, the BG level measured by the BG monitoring system 20 is used in a closed loop algorithm to automatically adjust the delivery of fluid, such as insulin, in the infusion pump 30. A calibration algorithm is used to convert sensor data into sensor measurements, and then the sensor measurements are used in a closed loop algorithm to generate fluid delivery commands to operate the infusion pump 30. In particular embodiments, the calibration algorithm 26 and closed loop algorithm 28 reside with and are executed by the processor of the BG monitoring system 20, as shown in FIG. 5(*a*). Commands to control the infusion pump 30 are generated at the BG monitoring system 20, and are sent through the relay device 10 to the infusion pump 30.

In other particular embodiments, the calibration algorithm 26 resides with and is executed by the processor of the BG monitoring system 20, and the closed loop algorithm 18 resides with and is executed by the processor of the relay device 10, as shown in FIG. 5(*b*). Calibrated sensor measurements are sent from the BG monitoring system 20 to the relay device 10, and fluid delivery commands are sent from the relay device to the infusion pump 30.

In still other particular embodiments, the calibration algorithm 26 resides with and is executed by the processor of the BG monitoring system 20, and the closed loop algorithm 38 resides with and is executed by the processor of the infusion pump 30, as shown in FIG. 5(*c*). Calibrated sensor measurements are sent from the BG monitoring system 20 through the relay device 10 to the infusion pump 30, and fluid delivery commands are generated at the infusion pump 30.

In yet other particular embodiments, the calibration algorithm 16 and the closed loop algorithm 18 both reside with and are executed by the processor of the relay device 10, as shown in FIG. 5(*d*). Uncalibrated sensor data is sent from the BG monitoring system 20 to the relay device 10, where they are calibrated and used in the closed loop algorithm 18 to generate fluid delivery commands, which are sent to the infusion pump 30.

In further particular embodiments, the calibration algorithm 16 resides with and is executed by the processor of the relay device 10, and the closed loop algorithm 38 resides with and is executed by the processor of the infusion pump 30, as shown in FIG. 5(*e*). Uncalibrated sensor data is sent from the BG monitoring system 20 to the relay device 10, where they are calibrated to generate sensor measurements. Then the sensor measurements are sent to the infusion pump 30 and used in the closed loop algorithm 38 to generate fluid delivery commands.

In additional particular embodiments, the calibration algorithm 36 and the closed loop algorithm 38 both reside with and are executed by the processor of the infusion pump 30, as shown in FIG. 5(*f*). Uncalibrated sensor data is sent from the BG monitoring system 20 through the relay device 10 to the infusion pump 30. Then, at the infusion pump 30, the uncalibrated sensor data is calibrated and used in the closed loop algorithm 38 to generate fluid delivery commands.

In alternative embodiments, a semi-closed loop algorithm is used in place of a closed loop algorithm. A semi-closed loop algorithm generates recommended changes to the fluid delivery, which must be approved by the user or a caregiver using the user interface on the infusion pump 30, the BG monitoring system 20, or the relay device 10 before new commands are issued to the infusion pump 30.

Although FIGS. 4(*a*)-5(*f*) generally show communication flowing from the BG monitoring system 20 to the infusion pump 30, it should be noted that communication signals might be generated by any of the devices. In particular embodiments, a signal may be sent from the infusion pump 30 through the relay device 10 to the BG monitoring system 20. The signals from the infusion pump 30 may include signals to request information from the BG monitoring system 20, verify receipt of information, echo information received, transmit information to be downloaded to the BG monitoring system 20, and the like. In additional alternative embodiments, signals may be initiated at the relay device 10 and sent to the BG monitoring system 20 and/or the infusion pump 30.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. An infusion system to infuse a fluid into a user, the infusion system comprising:
    a sensor system contained in a sensor housing that includes a sensor to produce a signal indicative of a physiological characteristic of the user, the sensor system further having a sensor processor to process the signal to sensor data, the sensor system further having a sensor receiver and a sensor transmitter, transmissions from the sensor transmitter being processed by the sensor processor and transmitted in a sensor system format;
    a relay system contained within a relay system housing that includes a first relay receiver to receive sensor data in the sensor system format and a second relay receiver, the relay system further having a relay system processor to convert the sensor system format to a delivery system format, the relay system further having a first relay transmitter to transmit sensor data in the delivery system format and a relay system user interface, the relay system user interface being used to control a second relay transmitter to transmit communications to the sensor receiver; and
    a delivery system contained within a delivery system housing that includes a delivery system receiver to receive transmissions from the first relay transmitter in the delivery system format, the communications received in the delivery system format being processed by a delivery system processor to determine an amount of fluid to be infused into the user, the delivery system further including a delivery system transmitter,
    wherein manipulation of the relay system user interface prompts the delivery system transmitter to send a request to the sensor system for sensor data through the second relay receiver and second relay transmitter, the relay system user interface further configured to send commands to the delivery system.

2. An infusion system according to claim 1, wherein the delivery system further includes:
    a display device contained within the delivery system housing, the display device being coupled to the delivery system processor to display data to the user; and
    a delivery system interface contained in the delivery system housing and coupled to the delivery system processor to accept at least one input from the user, wherein the at least one input causes the display device to display the sensor data transmitted through the relay system.

3. An infusion system according to claim 2,
    wherein manipulation of the delivery system interface prompts the delivery system transmitter to send a request to the sensor system through the second relay receiver.

4. An infusion system according to claim 2, where the delivery system interface is substantially similar to the relay system interface.

5. An infusion system according to claim 2, wherein the delivery system further includes an indication device that indicates when the sensor data received from the sensor system is above or below a target value.

6. An infusion system according to claim 1, wherein the sensor transmitter sends sensor data through the relay system to the delivery system.

7. An infusion system according to claim 1, wherein the sensor system automatically sends sensor data through the relay system to the delivery system at periodic intervals.

8. An infusion system according to claim 1 further including:
    a bolus estimator used in conjunction with the delivery system processor to estimate the amount of fluid to be infused into the user partially based upon the sensor data.

9. An infusion system according to claim 1, wherein the sensor system further includes a calibration algorithm, the calibration algorithm being executed by the sensor system processor to calibrate the sensor data.

10. An infusion system according to claim 1, wherein the sensor system format and the delivery system format utilize different communication protocols for transmissions from the sensor system through the relay device and received by the fluid delivery system.

11. A relay system to transmit between a sensor system and a delivery system, the relay system comprising:
    a relay system housing separate from the sensor system and the delivery system;
    a relay system processor contained within the relay system housing;
    a first relay receiver to receive sensor transmissions from the sensor system in a sensor system format, the relay receiver coupled to the relay system processor;
    a second relay receiver to receive delivery system transmissions from the delivery system;
    a first relay transmitter to transmit the sensor transmissions to the delivery system in a delivery system format, the first relay transmitter coupled to the relay system processor, the relay system processor converts the sensor transmissions from the sensor system format to the delivery system format;
    a second relay transmitter to transmit between the relay system and the sensor system;
    the delivery system further including a delivery system transmitter; and
    a relay system interface to prompt a transmission from the delivery system transmitter to the sensor system through the second relay receiver and second relay transmitter to initiate the sensor system to transmit another sensor transmission, the relay system interface further configured to send commands to the delivery system,
    wherein the delivery system delivers a quantity of fluid based on the sensor transmissions sent through the relay system.

12. A relay system according to claim 11, wherein the delivery system further includes:
    a display device contained within a delivery system housing, the display device being coupled to a delivery system processor to display data to the user; and
    a delivery system interface contained in the delivery system housing and coupled to the delivery system processor to accept at least one input from the user, wherein the at least one input causes the display device to display the sensor data transmitted through the relay system.

13. A relay system according to claim 12,
    wherein manipulation of the delivery system interface prompts the delivery system transmitter to send a request to the sensor system through the second relay receiver.

14. A relay system according to claim 12 further including:
a bolus estimator used in conjunction with the delivery system processor to estimate the amount of fluid to be infused into the user partially based upon the sensor data.

15. A relay system according to claim 12, where the delivery system interface is substantially similar to the relay system interface.

16. A relay system according to claim 11, wherein the sensor system format and the delivery system format utilize different communication protocols.

17. A relay system according to claim 11, wherein the sensor system automatically sends sensor data through the relay system to the delivery system at periodic intervals.

18. A relay system according to claim 11, wherein the delivery system further includes an indication device that indicates when the sensor data received from the sensor system is above or below a target value.

19. A relay system according to claim 11, wherein the sensor system further includes a calibration algorithm, the calibration algorithm being executed by a sensor system processor to calibrate the sensor data.

20. A relay system according to claim 11, wherein the sensor transmitter sends sensor data through the relay system to the delivery system.

* * * * *